United States Patent [19]
Hillman et al.

[11] Patent Number: 6,135,941
[45] Date of Patent: Oct. 24, 2000

[54] HUMAN IMMUNE SYSTEM ASSOCIATED MOLECULES

[75] Inventors: Jennifer L. Hillman, Mountain View; Preeti Lal, Sunnyvale; Y. Tom Tang, Sunnyvale; Henry Yue, Sunnyvale; Janice Au-Young, Berkeley; Neil C. Corley, Mountain View; Karl J. Guegler, Menlo Park; Mariah R. Baughn, San Jose, all of Calif.

[73] Assignee: Incyte Pharmaceuticals, Inc., Palo Alto, Calif.

[21] Appl. No.: 09/049,672

[22] Filed: Mar. 27, 1998

[51] Int. Cl.$^7$ .............................. C07H 21/04; C12Q 1/70
[52] U.S. Cl. ................... 531/23.1; 435/69.1; 435/7.1; 435/6; 514/2; 536/23.5; 530/300; 530/350
[58] Field of Search .................... 435/69.1–1, 7.1, 435/6; 514/2, 12–19, 300–345, 350–385, 412; 536/23.1–24.2, 23.5

[56] References Cited

U.S. PATENT DOCUMENTS 4,642,334  2/1987  Moore et al. ........................... 530/388

OTHER PUBLICATIONS

Leoni et al, The Primary Structure of the Fab Fragment of Protein KAU, a Monoclonal Immunoglobulin M Cold Agglutinin, J. Bio Chem. 266:2836–2842, Feb. 15, 1991.

Utans et al, Cloning and Characterization of Allograft Inflammatory Factor–1: A Novel Macrophage Factor Identified in Rat Cardiac Allografts with Chronic Rejection, J. Clin Invest. 95:2954–2962, Jun. 1995.

Ellison et al, The nucleotide sequence of a human immunoglobulin C–gamma–1 gene, Nucleic Acids Res (19982) 10:4071–4079, Jul. 1982.

Flanagan et al, Mechanism of Divergence and Convergence of the Human Immunoglobulin alpha–1 and Alpha–2 Constant Region Gene Sequences, Cell (1984) 36:681–688, Mar. 3, 1984.

Combriato et al, V–gamma and J–gamma–C–gamma gene segments of the human immunoglobulin gamma light chain locus are separated by 14kb and rearrange by a deletion mechanism, Eur. J. Immunol. (1991) 21:1513–1522, Apr. 1991.

Reuber et al, Isolation of Arabidopsis Genes That Differentiate between Resistance Responses Mediated by the RPS2 and RPM1 Disease Resistance Genes, Plant Cell 8:241–249 (Feb. 1996).

Vasicek et al., Structure and Expression of the Human Immunoglobulin–gamma Genes, J. Exp. Med. (1009) 172:609–620, Aug. 1990.

Tomlinson et al, The Repertoire of Human Germline V–H Sequences Reveals about Fifty Groups of V–H Segments with Different Hypervariable Loops, J. Mol. Biol (Aug. 1992) 227:776–798.

Silvain et al, A Human myeloma IgA with a hybrid heavy chain resulting from putative somatic gene conversion, Eur. J. Immunol. 23(2): 364–368 (Sep. 1993).

Shuford et al, Effect of Light Chain V Region Duplication on IgA Oligomerization and in Vivo Efficacy, Science 252: 724–727 (May 3, 1991).

Lewis et al, Rescue, Expression, and Analysis of a Neutralizing Human Anti–Hepatitis A Virus Monoclonal Antibody, J. Immunol. 151 (5): 2829–2838 (Sep. 1, 1993).

Morin et al, cDNA the immunoglobulin kappa chain if an Epstein–Barr virus–transformed human lymphoid cell line: Partial sequence determination and bacterial expression, PNAS 82 (20): 7025–702, Oct. 1985.

Friedman et al, Variable Region Gene Analysis of an Isotype–Switched (IgA) Variant of Chronic Lymphocytic Leukemia, Blood 80(9): 2287–2297 (Nov. 1, 1992).

Kawamura et al, GenBank Accession S05500, Jun. 7, 1990.

Burgess et al j Cell Biol vol. 111:2129–2138, 1990.

Lazar et al Mol Cell Biol vol. 8:1247, 1988.

Tao et al J Immunol vol 143 2595, 1989.

Alberts, B. et al., *Molecular Biology of the Cell*, Garland Publishing. Inc., New York, NY, pp. 1206–1213 and 1216–1217 (1994).

Krucken, J, et al., "Novel Gene Expressed in Spleen Cells Mediating Acquired Testosterone–Resistant Immunity to *Plasmodium chabaudi* Malaria", *Biochem. Biophys. Res. Comm.*, 230: 167–170 (1997).

Junghans, R.P. et al., "Anri–Tac–H, a Humanized Antibody to the Interleukin 2 Receptor with New Features for Immunotherapy in Malignant and Immune Disorders", *Cancer Res.*, 50 : 1495–1502 (1990).

Brown, P.S. et al., "Anti–Tac–H, a humanized antibody to the interleuin 2 receptor, prolongs primate cardiac allograft survival", *Proc. Natl. Acad Sci. USA*, 88: 2663–2667 (1991).

Carter, P. et al., "High Level *Escherichia Coli* Expression and Production of a Bivalent Humanized Antibody Fragment", *Biotechnology*, 10: 163–167 (1992).

Utans, U. et al., "Cloning and Characterization of Allograft Inflammatory Factor–1: A Novel Macrophage Factor Identified in Rat Cardiac Allografts with Chronic Rejection", *J. Clin. Invest.*, 95: 2954–2962 (1995).

Utans, U et al., "Allograft Inflammatory Factor–1", *Transplantation*, 61: 1387–1392 (1996).

Golub, E.S., *Immunology A Sysnthesis*, Sinauer Associates, Inc., Sunderland, MA, pp. 481 and 509–530 (1987).

Utans, . et al., (Direct Submission), GenBank Sequence Database (Accession 1122909), National Center for Biotechnology Information, National Library of Medicine, Bethesda, Maryland, 20894, (GI 1122909) (Submitted Jul. 29, 1996).

(List continued on next page.)

*Primary Examiner*—Julie Burke
*Attorney, Agent, or Firm*—Incyte Pharmaceuticals, Inc.

[57] ABSTRACT

The invention provides human immune system associated proteins (HISAP) and polynucleotides which identify and encode HISAP. The invention also provides expression vectors, host cells, antibodies, agonists, and antagonists. The invention also provides methods for treating or preventing disorders associated with expression of HISAP.

17 Claims, 3 Drawing Sheets

OTHER PUBLICATIONS

Utans, U. et al., (Direct Submission), GenBank Sequence Database (Accession U19713), National Center for Biotechnology Information, National Library of Medicine, Bethesda, Maryland, 20894, (GI 1122908; GI 1122909) (Jul. 29, 1996).

Krucken, J. et al., (Direct Submission), GenBank Sequence Database (Accession 1550785), National Center for Biotechnology Information, National Library of Medicine, Bethesda, Maryland,20894, (GI 1550785) (Sep. 19, 1997).

Krucken, J. et al., (Direct Submission), GenBank Sequence Database (Accession Y08026), National Center for Biotechnology Information, National Library of Medicine, Bethesda, maryland, 20894, (GI 1550784; GI 1550785) Sep. 19, 1997.

Golub, E.S., *Immunology a Synthesis,* Sinauer Associates, Inc., Sunderland, MA, pp. 113–115 (1987).

Lewis, A.P. et al., (Direct Submission), GenBank Sequence Database (Oct. 8, 1993) (Accession M87790), National Center for Biotechnology Information, National Library of Medicine, Bethesda, Maryland, 20894, (GI 185363; GI 185364).

Klobeck, H.G., (Direct Submission), GenBank Sequence Database (Accession X57811), National Center for Biotechnology Information, national Library of Medicine, Bethesda, maryland, 20894, (GI 33721; GI 33722) Nov. 4, 1994.

Klobeck, H.G., (Direct Submission), GenBank Sequence Database (Accession X57814), National Center for Biotechnology Information, National Library of Medicine, Bethesda, maryland,20894, (GI 33727; GI 33728) (Nov. 4, 1994).

FIGURE 1

```
1    MSGELSNRFQGGKAFGLLKARQERRLAEIN    1320068
1    MSQ--TRDLQGGKAFGLLKAQQEERLDEIN    GI 1122909

31   REFLCDQKYSDEENLPEKLTAFKEKYMEFD    1320068
29   KQFLDDPKYSSDEDLPSKLEGFKEKYMEFD    GI 1122909

61   LNNEGEIDLMSLKRMMEKLGVPKTHLEMKK    1320068
59   LNGNGDIDIMSLKRMLEKLGVPKTHLELKK    GI 1122909

91   MISEVTGGVSDTISYRDFVNMMLGKRSAVL    1320068
89   LIGEVSSGETFSYPDFLRMMLGKRSAIL     GI 1122909

121  KLVMMFEGKANESSPKPVGPPPERDIASLP    1320068
119  KMILMYEEKAREKE-KPTGPPAKKAISELP   GI 1122909
```

```
1    MGGFQRGKYGTMAEGR-----SEDNLS           2784232
1    MQKGETGKNLSSENPKQMGAPGFQGEQAMW        GI 1550785

23   ATP--PALRIILVGKTGC-GKSATGNSIL         2784232
31   VLPLYAEGLNTSLSQRKACVSDSMLPHLIL        GI 1550785

49   GQPVFESKLRAQSVTRTC-----QVKTGTWN       2784232
61   RLRGLQGPADAPAEAHPSGQDWDRQECHWQ        GI 1550785

75   ---GRKVLVVDTPS--------IFESQ-----      2784232
91   QHPGSEVLPVQAGGGACHQKLHFGQQNVGR        GI 1550785

91   ----ADTQELYKNI-----------GDCYLL       2784232
121  LAGGGGHPGYLQLRDPADRPWVRGDSPLL         GI 1550785

107  SAPGP--HVLLLVIQLGRFTAQDTVAIRKV        2784232
151  CAVGPWAHALLLVTQLGRFTMQDSQALAAV        GI 1550785
```

HUMAN IMMUNE SYSTEM ASSOCIATED MOLECULES

FIELD OF THE INVENTION

This invention relates to nucleic acid and amino acid sequences of human immune system associated proteins and to the use of these sequences in the diagnosis, treatment, and prevention of immune and cell proliferative disorders and infections.

BACKGROUND OF THE INVENTION

All vertebrates have developed sophisticated and complex immune systems that provide protection from viral, bacterial, fungal, and parasitic infections. A key feature of the immune system is its ability to specifically discriminate foreign molecules from self molecules. A foreign molecule, or antigen, elicits a cascade of events that constitute the immune response. The immune response coordinates the progressive selection, amplification, and activation of cellular defense mechanisms, ultimately leading to the destruction of the foreign pathogen.

There are two basic classes of immune response: cellular and humoral. The cellular immune response is mediated primarily by T-lymphocytes, or T-cells, which either directly destroy invading microorganisms or stimulate the activity of other immune cells. The cellular immune response is most effective against fungi, parasites, cancer cells, transplanted tissue, and intracellular viral infections. The humoral immune response is mediated primarily by B-lymphocytes, or B-cells, which secrete antibodies into the circulation. The humoral immune response is most effective against bacterial and extracellular viral infections. Antibodies, or immunoglobulins (Ig), bind to molecules on the surface of invading microorganisms which are then inactivated and targeted for destruction by downstream effectors.

The prototypical antibody is a tetramer consisting of two identical heavy polypeptide chains (H-chains) and two identical light polypeptide chains (L-chains) interlinked by disulfide bonds. This arrangement confers the characteristic Y-shape to antibody molecules. Antibodies are classified based on their H-chain composition. The five antibody classes, IgA, IgD, IgE, IgG and IgM, are defined by the $\alpha$, $\delta$, $\epsilon$, $\gamma$, and $\mu$ H-chain types, respectively. There are two types of L-chains, $\kappa$ and $\lambda$, either of which may associate as a pair with any H-chain pair. IgG, the most common class of antibody found in the circulation, is tetrameric, as described above, while the other classes of antibodies are generally variants or multimers of this basic structure.

H-chains and L-chains each contain an N-terminal variable region and a C-terminal constant region. The sequence of the constant region, which consists of about 110 amino acids in L-chains and about 330 or 440 amino acids in H-chains, is nearly identical among H- or L-chains of a particular class. On the other hand, the sequence of the variable region, which consists of about 110 amino acids, differs among H- or L-chains of a particular class. Within each H- and L-chain variable region are three hypervariable regions of extensive sequence diversity, each consisting of about 5 to 10 amino acids. In the antibody molecule, the H- and L-chain hypervariable regions come together to form the antigen binding site. (Alberts, B. et al. (1994) Molecular Biology of the Cell, Garland Publishing, New York, N.Y., pages 1206–1213 and 1216–1217.)

The immune system is capable of recognizing and responding to any foreign molecule that enters the body. Therefore, the immune system must be armed with a full repertoire of antibodies against all potential antigens. Such antibody diversity is generated by rearrangements of genomic DNA encoding variable and constant regions. In each B-cell, gene segments are joined together by site-specific recombination to form a complete gene encoding an H- or L-chain. Site-specific recombination occurs within highly conserved DNA sequences flanking each gene segment. Because there are hundreds of these segments to choose from, millions of different genes can be generated combinatorially. In addition, imprecise joining of these segments and an unusually high rate of somatic mutation within these segments further contribute to antibody diversification.

An individual B-cell produces identical antibodies that are expressed on the cell surface until the B-cell is stimulated by antigen to secrete these antibodies. Cell surface antibodies are associated with transmembrane proteins involved in signal transduction pathways such as kinase cascades. A candidate for such a transmembrane protein is the mouse immune associated protein 38 (IAP38), whose expression is correlated with immunity to malaria infection. IAP38 is a 38 kilodalton protein with two potential N-glycosylation sites and two putative transmembrane domains. (Krucken, J. et al. (1997) Biochem. Biophys. Res. Comm. 230:167–170.)

Recombinant DNA technology has enabled the production of antibodies engineered for use as therapeutic and diagnostic agents. For example, chimeric proteins and protein compositions comprising the variable regions of antibodies retain antigen-binding specificity but lack H-chain constant regions, which often complicate both in vivo and in vitro downstream applications. (Moore, K. W. and Zaffaroni, A., U.S. Pat. No. 4,642,334.) In addition, rodent antibodies directed against human proteins can be "humanized" by replacing their constant regions with those from human antibodies. (Junghans, R. P. et al. (1990) Cancer Res. 50:1495–1502.) The variable regions of these humanized antibodies recognize human proteins, e.g., disease-associated proteins, while the constant regions activate downstream effectors and prevent the antibodies themselves from being recognized as foreign in a human host. Humanized antibodies have proved to be effective therapeutic agents for the prevention of transplant rejection in primate model systems and for their anti-proliferative activity in breast tumor cell lines. (Brown, P. S. et al. (1991) Proc. Natl. Acad. Sci. USA 88:2663–2667.) In addition, large quantities of humanized antibodies can be produced and purified from bacterial expression systems. (Carter, P. et al. (1992) Biotechnology (NY) 10:163–167.)

T-cells fall into two classes: cytotoxic T-cells, which directly eliminate foreign invaders, and helper T-cells, which stimulate the activity of other immune cells. All T-cells express cell surface receptors that directly bind to antigens. Like antibodies, receptor diversity is generated by "gene shuffling" mechanisms. Unlike antibodies, however, these receptors recognize foreign peptide fragments presented on the surface of an infected cell. For example, a virus-infected cell will degrade viral proteins intracellularly and transport the resulting peptide fragments to the cell surface. The peptide fragments are presented to T-cells in the context of self-identifying proteins called major histocompatibility (MHC) proteins. Cytotoxic T-cells either signal the infected cell to undergo programmed cell death or directly lyse the infected cell. Helper T-cells trigger the activation and proliferation of other immune cells, such as B-cells or macrophages, by secreting signaling molecules such as cytokines. The essential role of helper-T cells in the immune response is demonstrated by the devastating effects of acquired immune deficiency syndrome (AIDS), in which the HIV retrovirus severely depletes the number of helper T-cells.

Rejection of transplanted tissue is mediated by T-cell recognition of foreign MHC molecules. Animal models have helped elucidate the molecular basis for the rejection of allografts, which are tissue transplants between two genetically dissimilar individuals of the same species. Rejection of heart transplants between two different rat strains is characterized by arteriosclerosis associated with blood vessels of the donor heart. Activated macrophages and T-cells from the transplant recipient infiltrate the vessel lumen and attract proliferating smooth muscle cells. This inflammatory response is correlated with increased expression of allograft inflammatory factor-1 (AIF-1) in activated macrophages. AIF-1 expression is stimulated by T-cell-derived cytokines such as IFN-γ. AIF-1 cDNA predicts a 147-amino acid protein of 16.8 kilodaltons. AIF-1 contains a single EF-hand calcium binding domain, although the functional relevance of this motif is unknown. A human AIF-1 homolog with 90% amino acid identity to the rat protein has been identified and may likewise play a key role in macrophage-mediated cardiac rejection. (Utans, U. et al. (1995) J. Clin. Invest. 95:2954–2962; Utans, U. et al. (1996) Transplantation 61:1387–1392.)

The major organs of the immune system are classified as either primary or secondary lymphoid organs. Primary lymphoid organs include the bone marrow, which produces B-cells, and the thymus, which produces T-cells. Upon maturation, B- and T-cells travel through the lymphatic system and populate secondary lymphoid organs throughout the body such as the lymph nodes, adenoids, tonsils, spleen, and intestinal Peyer's patches.

Disorders associated with the immune system, in addition to those discussed above, include various autoimmune diseases caused by failure of the immune system to discriminate self from non-self molecules. In addition, diseases associated with immune cell proliferation include multiple myeloma, in which antibody-secreting tumors develop from bone marrow cells. Immunodeficiency, brought on by a variety of diseases and agents including HIV, renders afflicted individuals susceptible to severe and sometimes fatal bacterial and viral infections. (Golub, E. S. et al. (1987) *Immunology: A Synthesis,* Sinauer Associates, Sunderland, Mass., pages 481 and 509–530.)

The discovery of new human immune system associated proteins and the polynucleotides encoding them satisfies a need in the art by providing new compositions which are useful in the diagnosis, treatment, and prevention of immune and cell proliferative disorders and infections.

SUMMARY OF THE INVENTION

The invention is based on the discovery of new human immune system associated proteins (HISAP), the polynucleotides encoding HISAP, and the use of these compositions for the diagnosis, treatment, or prevention of immune and cell proliferative disorders and infections. The invention features substantially purified polypeptides, human immune system associated proteins, referred to collectively as "HISAP" and individually as "HISAP-1," "HISAP-2," "HISAP-3," "HISAP4," "HISAP-5," "HISAP-6," "HISAP-7," "HISAP-8," "HISAP-9," "HISAP-10," "HISAP-1 1," "HISAP-12," and "HISAP-13." In one aspect, the invention provides a substantially purified polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 (SEQ ID NO:1 through 13), and fragments thereof.

The invention further provides a substantially purified variant having at least 90% amino acid identity to any of the amino acid sequences of SEQ ID NO:1 through 13, or to a fragment of any of these sequences. The invention also provides an isolated and purified polynucleotide encoding the polypeptide comprising an amino acid sequence selected from the group consisting of SEQ ID NO:1 through 13 and fragments thereof. The invention also includes an isolated and purified polynucleotide variant having at least 90% polynucleotide sequence identity to the polynucleotide encoding the polypeptide comprising an amino acid sequence selected from the group consisting of SEQ ID NO:1 through 13 and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1 through 13 and fragments thereof, as well as an isolated and purified polynucleotide having a sequence which is complementary to the polynucleotide encoding the polypeptide comprising the amino acid sequence selected from the group consisting of SEQ ID NO:1 through 13 and fragments thereof.

The invention also provides an isolated and purified polynucleotide comprising a polynucleotide sequence selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 (SEQ ID NO:14 through 26), and fragments thereof. The invention further provides an isolated and purified polynucleotide variant having at least 90% polynucleotide sequence identity to the polynucleotide sequence comprising a polynucleotide sequence selected from the group consisting of SEQ ID NO:14 through 26 and fragments thereof, as well as an isolated and purified polynucleotide having a sequence which is complementary to the polynucleotide sequence comprising a polynucleotide sequence selected from the group consisting of SEQ ID NO:14 through 26 and fragments thereof.

The invention further provides an expression vector containing at least a fragment of the polynucleotide encoding the polypeptide comprising an amino acid sequence selected from the group consisting of SEQ ID NO:1 through 13 and fragments thereof. In another aspect, the expression vector is contained within a host cell.

The invention also provides a method for producing a polypeptide comprising the amino acid sequence selected from the group consisting of SEQ ID NO:1 through 13 and fragments thereof, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1 through 13 and fragments thereof in conjunction with a suitable pharmaceutical carrier.

The invention further includes a purified antibody which binds to a polypeptide comprising the amino acid sequence selected from the group consisting of SEQ ID NO:1 through 13 and fragments thereof, as well as a purified agonist and a purified antagonist to the polypeptide.

The invention also provides a method for treating or preventing an immune disorder associated with decreased expression or activity of HISAP, the method comprising administering to a subject in need of such treatment an effective amount of a pharmaceutical composition comprising a substantially purified polypeptide having an amino acid sequence selected from the group consisting of SEQ ID NO:1 through 13 and fragments thereof.

The invention also provides a method for treating or preventing an immune disorder associated with increased expression or activity of HISAP, the method comprising administering to a subject in need of such treatment an effective amount of an antagonist of the polypeptide having an amino acid sequence selected from the group consisting of SEQ ID NO:1 through 13 and fragments thereof.

The invention also provides a method for treating or preventing a cell proliferative disorder, the method comprising administering to a subject in need of such treatment an effective amount of an antagonist of the polypeptide having an amino acid sequence selected from the group consisting of SEQ ID NO:1 through 13 and fragments thereof.

The invention also provides a method for treating or preventing an infection, the method comprising administering to a subject in need of such treatment an effective amount of a pharmaceutical composition comprising a substantially purified polypeptide having an amino acid sequence selected from the group consisting of SEQ ID NO:1 through 13 and fragments thereof.

The invention also provides a method for detecting a polynucleotide encoding the polypeptide comprising the amino acid sequence selected from the group consisting of SEQ ID NO:1 through 13 and fragments thereof in a biological sample containing nucleic acids, the method comprising the steps of: (a) hybridizing the complement of the polynucleotide sequence encoding the polypeptide comprising the amino acid sequence selected from the group consisting of SEQ ID NO:1 through 13 and fragments thereof to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIG. 1 shows the amino acid sequence alignment between HISAP-3 (1320068; SEQ ID NO:3) and human AIF-1 (GI 1122909; SEQ ID NO:27).

FIGS. 2A and 2B show the amino acid sequence alignment between HISAP-9 (2784232; SEQ ID NO:9) and mouse IAP38 (GI 1550785; SEQ ID NO:28). The alignments were produced using the multisequence alignment program of LASERGENE™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that, as used herein, and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HISAP," as used herein, refers to the amino acid sequences of substantially purified HISAP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HISAP, increases or prolongs the duration of the effect of HISAP. Agonists may include proteins, nucleic acids, carbohydrates, or any other molecules which bind to and modulate the effect of HISAP.

An "allele" or an "allelic sequence," as these terms are used herein, is an alternative form of the gene encoding HISAP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HISAP, as described herein, include those sequences with deletions, insertions, or substitutions of different nucleotides, resulting in a polynucleotide the same HISAP or a polypeptide with at least one functional characteristic of HISAP. Included within this definition are polymorphisms which may or may not be readily detectable using a particular oligonucleotide probe of the polynucleotide encoding HISAP, and improper or unexpected hybridization to alleles, with a locus other than the normal chromosomal locus for the polynucleotide sequence encoding HISAP. The encoded protein may also be "altered," and may contain deletions, insertions, or substitutions of amino acid residues which produce a silent change and result in a functionally equivalent HISAP. Deliberate amino acid substitutions may be made on the basis of similarity in polarity, charge, solubility, hydrophobicity, hydrophilicity, and/or the amphipathic nature of the residues, as long as the biological or immunological activity of HISAP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HISAP which are preferably about 5 to about 15 amino acids in length and which retain some biological activity or immunological activity of HISAP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp.1–5.)

The term "antagonist," as it is used herein, refers to a molecule which, when bound to HISAP, decreases the amount or the duration of the effect of the biological or immunological activity of HISAP. Antagonists may include proteins, nucleic acids, carbohydrates, antibodies, or any other molecules which decrease the effect of HISAP.

As used herein, the term "antibody" refers to intact molecules as well as to fragments thereof, such as Fa, F(ab')$_2$, and Fv fragments, which are capable of binding the epitopic determinant. Antibodies that bind HISAP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HISAP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HISAP or fragments of HISAP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HISAP, by northern analysis is indicative of the presence of nucleic acids encoding HISAP in a sample, and thereby correlates with expression of the transcript from the polynucleotide encoding HISAP.

A "deletion," as the term is used herein, refers to a change in the amino acid or nucleotide sequence that results in the absence of one or more amino acid residues or nucleotides.

The term "derivative," as used herein, refers to the chemical modification of HISAP, of a polynucleotide sequence encoding HISAP, or of a polynucleotide sequence complementary to a polynucleotide sequence encoding HISAP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one. biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule. "Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HISAP. For example, modulation may cause an increase or a decrease in protein activity, binding characteristics, or any other biological, functional, or immunological properties of HISAP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art. "Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.) The term "sample," as used herein, is used in its broadest sense. A biological sample suspected of containing nucleic acids encoding HISAP, or fragments thereof, or HISAP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively. "Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HISAP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

THE INVENTION

The invention is based on the discovery of new human immune system associated proteins (HISAP), the polynucleotides encoding HISAP, and the use of these compositions for the diagnosis, treatment, or prevention of immune and cell proliferative disorders and infections. Table 1 shows the protein and nucleotide sequence identification numbers, Incyte Clone identification number, and cDNA library for each of the human immune system associated proteins disclosed herein.

TABLE 1

| Protein | Nucleotide | Clone ID | Library |
| --- | --- | --- | --- |
| SEQ ID NO:1 | SEQ ID NO:14 | 021145 | ADENINB01 |
| SEQ ID NO:2 | SEQ ID NO:15 | 161752 | ADENINB01 |
| SEQ ID NO:3 | SEQ ID NO:16 | 1320068 | BLADNOT04 |
| SEQ ID NO:4 | SEQ ID NO:17 | 1513264 | PANCTUT01 |
| SEQ ID NO:5 | SEQ ID NO:18 | 1669829 | BMARNOT03 |
| SEQ ID NO:6 | SEQ ID NO:19 | 2280869 | COLSUCT01 |
| SEQ ID NO:7 | SEQ ID NO:20 | 2492122 | ADRETUT05 |
| SEQ ID NO:8 | SEQ ID NO:21 | 2747531 | LUNGTUT11 |
| SEQ ID NO:9 | SEQ ID NO:22 | 2784232 | BRSTNOT13 |
| SEQ ID NO:10 | SEQ ID NO:23 | 2872705 | THYRNOT10 |
| SEQ ID NO:11 | SEQ ID NO:24 | 3056213 | LNODNOT08 |
| SEQ ID NO:12 | SEQ ID NO:25 | 3116314 | LUNGTUT13 |
| SEQ ID NO:13 | SEQ ID NO:26 | 3551457 | SYNONOT01 |

Nucleic acids encoding the HISAP-1 of the present invention were first identified in Incyte Clone 021145 from the adenoid cDNA library (ADENINB01) using a computer search for amino acid sequence alignments. A consensus sequence, SEQ ID NO:14, was derived from the following overlapping and/or extended nucleic acid sequences: Incyte Clones 021145 (ADENINB01), 2746667 (LUNGTUT11), 1298248 (BRSTNOT07), 1242278, (LUNGNOT03), 1005028, 1001758, and 1005167 (BRSTNOT03), 1216413 (BRSTTUT01), and 1208529 (BRSTNOT02).

In one embodiment, the invention encompasses a polypeptide comprising the amino acid sequence of SEQ ID NO:1. HISAP-1 is 499 amino acids in length and has three potential N-glycosylation sites at N290, N364, and N486; one potential cAMP- and cGMP-dependent protein kinase phosphorylation site at S81; six potential casein kinase II phosphorylation sites at T22, T104, T162, T186, S402, and S427; and nine potential protein kinase C phosphorylation sites at T22, S83, T94, S151, T195, S312, T371, S402, and T471. Protein sequence analysis using various search algorithms indicates that regions of HISAP-1 show strong homology to Ig domains. Motifs analysis indicates that HISAP-1 contains two Ig/MHC complex protein signatures from F348 to H354 and from F457 to H463. BLOCKS analysis indicates that HISAP-1 contains both of the conserved protein domain blocks found in Ig and MHC proteins. These blocks extend from T393 to Q415 and from F457 to T474.

Hidden Markov Model analysis indicates that HISAP-1 contains three regions with similarity to Ig superfamily protein domains from T34 to H118, from G286 to A352, and from N389 to V461. BLAST analyses indicate that the region of HISAP-1 from S148 to its C-terminus shows significant amino acid identity to the a H-chain constant region of primate immunoglobulins. Two independent search algorithms also predict a signal peptide sequence in HISAP-1 from M1 to S19. A region of unique sequence in HISAP-1 from about amino acid H118 to about amino acid Q131 is encoded by a fragment of SEQ ID NO:14 from about nucleotide 402 to about nucleotide 443. Northern analysis shows the expression of this sequence in various libraries, at least 61% of which are associated with cell proliferation and at least 40% are associated with the immune response.

Nucleic acids encoding the HISAP-2 of the present invention were first identified in Incyte Clone 161752 from the adenoid cDNA library (ADENINB01) using a computer search for amino acid sequence alignments. A consensus sequence, SEQ ID NO:15, was derived from the following overlapping and/or extended nucleic acid sequences: Incyte Clones 161752 (ADENINB01), 736124 (TONSNOT01), and 077225 (SYNORAB01).

In one embodiment, the invention encompasses a polypeptide comprising the amino acid sequence of SEQ ID NO:2. HISAP-2 is 234 amino acids in length and has one potential N-glycosylation site at N40; six potential casein kinase II phosphorylation sites at T18, T34, T122, S182, T184, and S202; and two potential protein kinase C phosphorylation sites at S42 and S79. Protein sequence analysis using various search algorithms indicates that regions of HISAP-2 show strong homology to Ig domains. Motifs analysis indicates that HISAP-2 contains one Ig/MHC complex protein signature from Y212 to H218. BLOCKS analysis indicates that HISAP-2 contains both of the conserved protein domain blocks found in Ig and MHC proteins. These blocks extend from S151 to A173 and from Y212 to F229. Hidden Markov Model analysis indicates that HISAP-2 contains two regions with similarity to Ig superfamily protein domains from G36 to Q110 and from S147 to V216. BLAST analyses indicate that HISAP-2 shows significant amino acid identity to vertebrate immunoglobulin κ L-chain. Two independent search algorithms also predict a signal peptide sequence in HISAP-2 from M1 to A20. A region of unique sequence in HISAP-2 from about amino acid P28 to about amino acid G36 is encoded by a fragment of SEQ ID NO:15 from about nucleotide 124 to about nucleotide 150. Northern analysis shows the expression of this sequence in various libraries, at least 60% of which are associated with cell proliferation and at least 40% are associated with the immune response.

Nucleic acids encoding the HISAP-3 of the present invention were first identified in Incyte Clone 1320068 from the bladder cDNA library (BLADNOT04) using a computer search for amino acid sequence alignments. A consensus sequence, SEQ ID NO:16, was derived from the following overlapping and/or extended nucleic acid sequences: Incyte Clones 1320068 (BLADNOT04), 2449282 (ENDANOT01), 2621589 (KERANOT02), 2202678 (SPLNFET02), 1440814 (THYRNOT03), 268916 (HNT2NOT01), 1593994 (BRAINOT14), 1479032 (CORPNOT02), 1642330 (HEARFET01), and 1422044 (KIDNNOT09).

In one embodiment, the invention encompasses a polypeptide comprising the amino acid sequence of SEQ ID NO:3. HISAP-3 is 150 amino acids in length and has one potential N-glycosylation site at N131; three potential casein kinase II phosphorylation sites at S40, T84, and S104; and four potential protein kinase C phosphorylation sites at S6, S71, S104, and S134. As shown in FIG. 1, HISAP-3 has chemical and structural homology with human AIF-1 (GI 1122909; SEQ ID NO:27). In particular, HISAP-3 and AIF-1 share 62% identity. Eight of the twelve amino acids comprising the EF-hand motif in AIF-1 are conserved in HISAP-3. The potential phosphorylation sites at S40, T84, S104, and S71 in HISAP-3 are conserved in AIF-1. A region of unique sequence in HISAP-3 from about amino acid S2 to about amino acid Q10 is encoded by a fragment of SEQ ID NO:16 from about nucleotide 102 to about nucleotide 128. Northern analysis shows the expression of this sequence in various libraries, at least 62% of which are associated with cell proliferation and at least 35% of which are associated with the immune response.

Nucleic acids encoding the HISAP-4 of the present invention were first identified in Incyte Clone 1513264 from the pancreatic tumor cDNA library (PANCTUT01) using a computer search for amino acid sequence alignments. A consensus sequence, SEQ ID NO:17, was derived from the following overlapping and/or extended nucleic acid sequences: Incyte Clones 1513264 (PANCTUT01), 3235001 (COLNUCT03), 792129 (PROSTUT03), 023700 (ADENINB01), 029692 (SPLNFET01), 1237286 (LUNGTUT02), and 081036 and 081086 (SYNORAB01).

In one embodiment, the invention encompasses a polypeptide comprising the amino acid sequence of SEQ ID NO:4. HISAP-4 is 473 amino acids in length and has one potential N-glycosylation site at N323; four potential casein kinase II phosphorylation sites at T 107, T235, S293, and S380; eight potential protein kinase C phosphorylation sites at S83, T94, S100, S145, S157, T325, S350, and T463; and two potential tyrosine kinase phosphorylation sites at Y71 and Y322. Protein sequence analysis using various search algorithms indicates that regions of HISAP-4 show strong homology to Ig domains. Motifs analysis indicates that HISAP4 contains two Ig/MHC complex protein signatures from Y224 to H230 and from F449 to H455. BLOCKS analysis indicates that HISAP-4 contains both of the conserved protein domain blocks found in Ig and MHC proteins. These blocks extend from S390 to G412 and from F449 to S466. Hidden Markov Model analysis indicates that HISAP-4 contains three regions with similarity to Ig superfamily protein domains from S34 to R118, from G163 to V228, and from K386 to V453. BLAST analyses indicate that HISAP-4 shows significant amino acid identity to vertebrate immunoglobulin γ H-chain. Two independent search algorithms also predict a signal peptide sequence in HISAP-4 from M1 to S19. A region of unique sequence in HISAP-4 from about amino acid D119 to about amino acid M130 is encoded by a fragment of SEQ ID NO:17 from about nucleotide 432 to about nucleotide 467. Northern analysis shows the expression of this sequence in various libraries, at least 61% of which are associated with cell proliferation and at least 38% are associated with the immune response.

Nucleic acids encoding the HISAP-5 of the present invention were first identified in Incyte Clone 1669829 from the bone marrow cDNA library (BMARNOT03) using a computer search for amino acid sequence alignments. A consensus sequence, SEQ ID NO:18, was derived from the following overlapping and/or extended nucleic acid sequences: Incyte Clones 1669829 (BMARNOT03), 171771 (BMARNOR02), 1216413 (BRSTTUT01), 1001531 (BRSTNOT03), 1630564 (COLNNOT19), 1208529 (BRSTNOT02), and shotgun sequence SAEA02768.

In one embodiment, the invention encompasses a polypeptide comprising the amino acid sequence of SEQ ID NO:5. HISAP-5 is 483 amino acids in length and has four potential N-glycosylation sites at N190, N274, N348, and N470; five potential casein kinase II phosphorylation sites at T47, T159, T183, S386, and S411; and ten potential protein kinase C phosphorylation sites at S36, S82, S104, T121, S148, T192, S296, T355, S386, and T455. Protein sequence analysis using various search algorithms indicates that regions of HISAP-5 show strong homology to Ig domains. Motifs analysis indicates that HISAP-5 contains two Ig/MHC complex protein signatures from F332 to H338 and from P441 to H447. BLOCKS analysis indicates that HISAP-5 contains both of the conserved protein domain blocks found in Ig and MHC proteins. These blocks extend from T377 to Q399 and from F441 to T458. Hidden Markov Model analysis indicates that HISAP-5 contains three regions with similarity to Ig superfamily protein domains from G34 to A111, from G270 to A336, and from N373 to V445. BLAST analyses indicate that HISAP-5 shows significant amino acid identity to the a H-chain constant region of primate immunoglobulins. Two independent search algorithms also predict a signal peptide sequence in HISAP-5 from M1 to C19. A region of unique sequence in HISAP-5 from about amino acid L119 to about amino acid M130 is encoded by a fragment of SEQ ID NO:18 from about nucleotide 418 to about nucleotide 453. Northern analysis shows the expression of this sequence in various libraries, at least 62% of which are associated with cell proliferation and at least 38% are associated with the immune response.

Nucleic acids encoding the HISAP-6 of the present invention were first identified in Incyte Clone 2280869 from the sigmoid colon cDNA library (COLSUCT01) using a computer search for amino acid sequence alignments. A consensus sequence, SEQ ID NO:19, was derived from the following overlapping and/or extended nucleic acid sequences: Incyte Clones 2280869 (COLSUCT01), 1435533 (PANCNOT08), and 077225 (SYNORAB01).

In one embodiment, the invention encompasses a polypeptide comprising the amino acid sequence of SEQ ID NO:6. HISAP-6 is 234 amino acids in length and has six potential casein kinase II phosphorylation sites at S 18, S34, S87, S182, T184, and S202 and three potential protein kinase C phosphorylation sites at S42, S63, and S72. Protein sequence analysis using various search algorithms indicates that regions of HISAP-6 show strong homology to Ig domains. Motifs analysis indicates that HISAP-6 contains one Ig/MHC complex protein signature from Y212 to H218. BLOCKS analysis indicates that HISAP-6 contains both of the conserved protein domain blocks found in Ig and MHC proteins. These blocks extend from S151 to A173 and from Y212 to F229. Hidden Markov Model analysis indicates that HISAP-6 contains two regions with similarity to Ig superfamily protein domains from G36 to Q110 and from S147 to V216. BLAST analyses indicate that HISAP-6 shows significant amino acid identity to human immunoglobulin κ L-chain. Two independent search algorithms also predict a signal peptide sequence in HISAP-6 from M1 to G20. A region of unique sequence in HISAP-6 from about amino acid Y111 to about amino acid T117 is encoded by a fragment of SEQ ID NO:19 from about nucleotide 346 to about nucleotide 366. Northern analysis shows the expression of this sequence in various libraries, at least 60% of which are associated with cell proliferation and at least 40% are associated with the immune response.

Nucleic acids encoding the HISAP-7 of the present invention were first identified in Incyte Clone 2492122 from the adrenal tumor cDNA library (ADRETUT05) using a computer search for amino acid sequence alignments. A consensus sequence, SEQ ID NO:20, was derived from the following overlapping and/or extended nucleic acid sequences: Incyte Clones 2492122 (ADRETUT05), 1438740 (PANCNOT08), and 137036 and 077057 (SYNORABO01).

In one embodiment, the invention encompasses a polypeptide comprising the amino acid sequence of SEQ ID NO:7. HISAP-7 is 236 amino acids in length and has two potential casein kinase II phosphorylation sites at S145 and S224 and one potential protein kinase C phosphorylation site at S211. Protein sequence analysis using various search algorithms indicates that regions of HISAP-7 show strong homology to Ig domains. Motifs analysis indicates that HISAP-7 contains one Ig/MHC complex protein signature from Y215 to H221. BLOCKS analysis indicates that HISAP-7 contains both of the conserved protein domain blocks found in Ig and MHC proteins. These blocks extend from T155 to S177 and from Y215 to P232. Hidden Markov Model analysis indicates that HISAP-7 contains two regions with similarity to Ig superfamily protein domains from G34 to S111 and from A151 to V219. BLAST analyses indicate that HISAP-7 shows significant amino acid identity to human immunoglobulin λ L-chain. Two independent search algorithms also predict a signal peptide sequence in HISAP-7 from M1 to A19. A region of unique sequence in HISAP-7 from about amino acid I69 to about amino acid R75 is encoded by a fragment of SEQ ID NO:20 from about nucleotide 278 to about nucleotide 298. Northern analysis shows the expression of this sequence in various libraries, at least 58% of which are associated with cell proliferation and at least 40% are associated with the immune response.

Nucleic acids encoding the HISAP-8 of the present invention were first identified in Incyte Clone 2747531 from the lung tumor cDNA library (LUNGTUT11) using a computer search for amino acid sequence alignments. A consensus sequence, SEQ ID NO:21, was derived from the following overlapping and/or extended nucleic acid sequences: Incyte Clones 2747531 (LUNGTUT11), 841102 (PROSTUT05), 136013 and 079552 (SYNORAB01), and 365750 (SYNORAT01).

In one embodiment, the invention encompasses a polypeptide comprising the amino acid sequence of SEQ ID NO:8. HISAP-8 is 467 amino acids in length and has one potential N-glycosylation site at N317; seven potential casein kinase II phosphorylation sites at S26, T47, T88, T93, T229, S287, and S374; six potential protein kinase C phosphorylation sites at T4, S139, S151, T319, S344, and T457; and one potential tyrosine kinase phosphorylation site at Y316. Protein sequence analysis using various search algorithms indicates that regions of HISAP-8 show strong homology to Ig domains. Motifs analysis indicates that HISAP-8 contains two Ig/MHC complex protein signatures from Y218 to H224 and from F443 to H449. BLOCKS analysis indicates that HISAP-8 contains both of the conserved protein domain blocks found in Ig and MHC proteins. These blocks extend from S384 to Q406 and from F443 to S460. Hidden Markov Model analysis indicates that HISAP-8 contains three regions with similarity to Ig superfamily protein domains from G34 to R117, from G157 to V222, and from K380 to V447. BLAST analyses indicate that HISAP-8 shows significant amino acid identity to vertebrate immunoglobulin γ H-chain. Two independent search algorithms also predict a signal peptide sequence in HISAP-8 from M1 to A19. A region of unique sequence in HISAP-8 from about amino acid G69 to about amino acid Y79 is encoded by a fragment of SEQ ID NO:21 from about nucleotide 251 to about nucleotide 283. Northern analysis shows the expression of this sequence in various libraries, at least 61% of which are associated with cell proliferation and at least 38% are associated with the immune response.

Nucleic acids encoding the HISAP-9 of the present invention were first identified in Incyte Clone 2784232 from the breast cDNA library (BRSTNOT13) using a computer search for amino acid sequence alignments. A consensus sequence, SEQ ID NO:22, was derived from the following overlapping and/or extended nucleic acid sequences: Incyte Clones 2784232 (BRSTNOT13), 2238123 (PANCTUT02), 077727 (SYNORAB01), 776108 (COLNNOT05), and 1447764 (PLACNOT02).

In one embodiment, the invention encompasses a polypeptide comprising the amino acid sequence of SEQ ID NO:9. HISAP-9 is 307 amino acids in length and has three potential N-glycosylation sites at N20, N170, and N263; seven potential casein kinase II phosphorylation sites at T11, S85, S89, T124, T151, S172, and S192; two potential protein kinase C phosphorylation sites at T151 and S172; one potential tyrosine kinase phosphorylation site at Y184; and an ATP/GTP-binding site motif A (P-loop) from G34 to S41. As shown in FIGS. 2A and 2B, HISAP-9 has chemical and structural homology with mouse IAP38 (GI 1550785; SEQ ID NO:28). In particular, HISAP-9 and IAP38 share 25% identity. In addition, the region of HISAP-9 from G101 to F224 shares 50% identity with the corresponding region in IAP38. Hydrophobicity analyses indicate that the two putative transmembrane domains in IAP38 are conserved in HISAP-9 from about L105 to about L120 and from about E284 to about I299. BLOCKS analysis also indicates that the region of HISAP-9 from about L280 to about Y306 shows conservation with transmembrane domains of both the connexin protein family and the transmembrane 4 protein family. Furthermore, BLOCKS and PRINTS analyses indicate that the region of HISAP-9 from L79 to Y97 and the overlapping region from Q90 to K133 show conservation with protein kinase regulatory subunits. In addition, the potential phosphorylation sites at T124, T151, and S192 in HISAP-9 are conserved in IAP38. A region of unique sequence in HISAP-9 from about amino acid G49 to about amino acid R58 is encoded by a fragment of SEQ ID NO:22 from about nucleotide 446 to about nucleotide 475. Northern analysis shows the expression of this sequence in various libraries, at least 43% of which are associated with cell proliferation and at least 59% of which are associated with the immune response.

Nucleic acids encoding the HISAP-10 of the present invention were first identified in Incyte Clone 2872705 from the thyroid cDNA library (THYRNOT10) using a computer search for amino acid sequence alignments. A consensus sequence, SEQ ID NO:23, was derived from the following overlapping and/or extended nucleic acid sequences: Incyte Clones 2872705 (THYRNOT10), 1453669 (PENITUT01), 137659 (SYNORAB01), and 1241315 (LUNGNOT03).

In one embodiment, the invention encompasses a polypeptide comprising the amino acid sequence of SEQ ID NO:10. HISAP-10 is 235 amino acids in length and has three potential casein kinase II phosphorylation sites at T44, S144, and S223 and three potential protein kinase C phosphorylation sites at S73, S80, and S210. Protein sequence analysis using various search algorithms indicates that regions of HISAP-10 show strong homology to Ig domains. Motifs analysis indicates that HISAP-10 contains one Ig/MHC complex protein signature from Y214 to H220. BLOCKS analysis indicates that HISAP-10 contains both of the conserved protein domain blocks found in Ig and MHC proteins. These blocks extend from T154 to S176 and from Y214 to P231. Hidden Markov Model analysis indicates that HISAP-10 contains two regions with similarity to Ig superfamily protein domains from G34 to S111 and from A150 to V218. BLAST analyses indicate that HISAP-10 shows significant amino acid identity to human immunoglobulin λ L-chain. Two independent search algorithms also predict a signal peptide sequence in HISAP-10 from M1 to A19. A region of unique sequence in HISAP-10 from about amino acid C109 to about amino acid V118 is encoded by a fragment of SEQ ID NO:23 from about nucleotide 358 to about nucleotide 387. Northern analysis shows the expression of this sequence in various libraries, at least 59% of which are associated with cell proliferation and at least 38% are associated with the immune response.

Nucleic acids encoding the HISAP-11 of the present invention were first identified in Incyte Clone 3056213 from the peripancreatic lymph node cDNA library (LNODNOT08) using a computer search for amino acid sequence alignments. A consensus sequence, SEQ ID NO:24, was derived from the following overlapping and/or extended nucleic acid sequences: Incyte Clones 3056213 (LNODNOT08), 2618575 (GBLANOTO01) and 077057 (SYNORAB01).

In one embodiment, the invention encompasses a polypeptide comprising the amino acid sequence of SEQ ID NO:11. HISAP-11 is 240 amino acids in length and has three potential casein kinase II phosphorylation sites at S20, S149, and S228 and two potential protein kinase C phosphorylation sites at S78 and S215. Protein sequence analysis using various search algorithms indicates that regions of HISAP-11 show strong homology to Ig domains. Motifs analysis indicates that HISAP-11 contains one Ig/MHC complex protein signature from Y219 to H225. BLOCKS analysis indicates that HISAP-11 contains both of the conserved protein domain blocks found in Ig and MHC proteins. These blocks extend from T159 to S181 and from Y219 to P236. Hidden Markov Model analysis indicates that HISAP-11 contains two regions with similarity to Ig superfamily protein domains from G39 to L116 and from A155 to V223. BLAST analyses indicate that HISAP-11 shows significant amino acid identity to human immunoglobulin λ L-chain. Two independent search algorithms also predict a signal peptide sequence in HISAP-11 from M1 to S24. A region of unique sequence in HISAP-11 from about amino acid Y117 to about amino acid F125 is encoded by a fragment of SEQ ID NO:24 from about nucleotide 396 to about nucleotide 419. Northern analysis shows the expression of this sequence in various libraries, at least 57% of which are associated with cell proliferation and at least 41% are associated with the immune response.

Nucleic acids encoding the HISAP-12 of the present invention were first identified in Incyte Clone 3116314 from the lung tumor cDNA library (LUNGTUT13) using a computer search for amino acid sequence alignments. A consensus sequence, SEQ ID NO:25, was derived from the following overlapping and/or extended nucleic acid sequences: Incyte Clones 3116314 (LUNGTUT13), and 081555 and 077057 (SYNORAB01).

In one embodiment, the invention encompasses a polypeptide comprising the amino acid sequence of SEQ ID NO:12. HISAP-12 is 235 amino acids in length and has three potential casein kinase II phosphorylation sites at T110, S144, and S223; one potential protein kinase C phosphorylation site at S210; and one potential tyrosine kinase phosphorylation site at Y106. Protein sequence analysis using various search algorithms indicates that regions of HISAP-12 show strong homology to Ig domains. Motifs analysis indicates that HISAP-12 contains one Ig/MHC complex protein signature from Y214 to H220. BLOCKS analysis indicates that HISAP-12 contains both of the conserved protein domain blocks found in Ig and MHC proteins. These blocks extend from T154 to S176 and from Y214 to P231. Hidden Markov Model analysis indicates that HISAP-12 contains two regions with similarity to Ig superfamily protein domains from G34 to T110 and from A150 to V218. BLAST analyses indicate that HISAP-12 shows significant amino acid identity to human immunoglobulin λ L-chain. Two independent search algorithms also predict a signal peptide sequence in HISAP-12 from M1 to A19. A region of unique sequence in HISAP-12 from about amino acid G43 to about amino acid A63 is encoded by a fragment of SEQ ID NO:25 from about nucleotide 163 to about nucleotide 225. Northern analysis shows the expression of this sequence in various libraries, at least 59% of which are associated with cell proliferation and at least 39% are associated with the immune response.

Nucleic acids encoding the HISAP-13 of the present invention were first identified in Incyte Clone 3551457 from the synovial cDNA library (SYNONOT01) using a computer search for amino acid sequence alignments. A consensus sequence, SEQ ID NO:26, was derived from the following overlapping and/or extended nucleic acid sequences: Incyte Clones 3551457 (SYNONOT01), 1578488 (DUODNOT01), and 1532791 (SPLNNOT04).

In one embodiment, the invention encompasses a polypeptide comprising the amino acid sequence of SEQ ID NO:13. HISAP-13 is 236 amino acids in length and has one potential cAMP- and cGMP-dependent protein kinase phosphorylation site at S194; four potential casein kinase II phosphorylation sites at S26, T124, T155, and T176; eight potential protein kinase C phosphorylation sites at T4, S36, S40, S104, S144, T155, T189, and T207; and one potential tyrosine kinase phosphorylation site at Y113. Protein sequence analysis using Hidden Markov Models indicates that HISAP-13 contains one region with similarity to Ig superfamily protein domains from G34 to R117. BLAST analyses indicate that HISAP-13 shows significant amino acid identity to human immunoglobulin μ H-chain variable region. A potential signal peptide sequence in HISAP-13 extends from M1 to S19. A region of unique sequence in HISAP-13 from about amino acid W119 to about amino acid F126 is encoded by a fragment of SEQ ID NO:26 from about nucleotide 389 to about nucleotide 412. Northern analysis shows the expression of this sequence in various libraries, at least 60% of which are associated with cell proliferation and at least 42% are associated with the immune response.

The invention also encompasses HISAP variants. A preferred HISAP variant is one which has at least about 80%, more preferably at least about 90%, and most preferably at least about 95% amino acid sequence identity to the HISAP amino acid sequence, and which contains at least one functional or structural characteristic of HISAP.

The invention also encompasses polynucleotides which encode HISAP. In a particular embodiment, the invention encompasses a polynucleotide sequence comprising a sequence selected from the group consisting of SEQ ID NO:14 through 26, which encodes an HISAP.

The invention also encompasses a variant of a polynucleotide sequence encoding HISAP. In particular, such a variant polynucleotide sequence will have at least about 80%, more preferably at least about 90%, and most preferably at least about 95% polynucleotide sequence identity to the polynucleotide sequence encoding HISAP. A particular aspect of the invention encompasses a variant of a polynucleotide sequence selected from the group consisting of SEQ ID NO:14 through 26 which has at least about 80%, more preferably at least about 90%, and most preferably at least about 95% polynucleotide sequence identity to a polynucleotide sequence selected from the group consisting of SEQ ID NO:14 through 26. Any one of the polynucleotide variants described above can encode an amino acid sequence which contains at least one functional or structural characteristic of HISAP.

It will be appreciated by those skilled in the art that as a result of the degeneracy of the genetic code, a multitude of polynucleotide sequences encoding HISAP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HISAP, and all such variations are to be considered as being specifically disclosed.

Although nucleotide sequences which encode HISAP and its variants are preferably capable of hybridizing to the nucleotide sequence of the naturally occurring HISAP under appropriately selected conditions of stringency, it may be advantageous to produce nucleotide sequences encoding HISAP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HISAP and its derivatives without altering the encoded amino acid sequences include the production of RNA transcripts having more desirable properties, such as a greater half-life, than transcripts produced from the naturally occurring sequence.

The invention also encompasses production of DNA sequences which encode HISAP and HISAP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HISAP or any fragment thereof.

Also encompassed by the invention are polynucleotide sequences that are capable of hybridizing to the claimed polynucleotide sequences, and, in particular, to any of those shown in SEQ ID NO:14 through 26 or a fragment of any of these sequences under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (U.S. Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (GIBCO/BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HISAP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055-306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO 4.06™ Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HISAP may be cloned in recombinant DNA molecules that direct expression of HISAP, or fragments or functional equivalents thereof, in appropriate host cells. Due to the inherent degeneracy of the genetic code, other DNA sequences which encode substantially the same or a functionally equivalent amino acid sequence may be produced and used to express HISAP.

The nucleotide sequences of the present invention can be engineered using methods generally known in the art in order to alter HISAP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HISAP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, HISAP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431 A Peptide Synthesizer (Perkin Elmer). Additionally, the amino acid sequence of HISAP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties,* W H Freeman and Co., New York, N.Y.)

In order to express a biologically active HISAP, the nucleotide sequences encoding HISAP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HISAP. Such elements may vary in their strength and specificity. Specific initiation signals may also be used to achieve more efficient translation of sequences encoding HISAP. Such signals include the ATG initiation codon and adjacent sequences, e.g. the Kozak sequence. In cases where sequences encoding HISAP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HISAP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HISAP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HISAP. For example, routine cloning, subcloning, and propagation of polynucleotide sequences encoding HISAP can be achieved using a multifunctional *E. coli* vector such as Bluescript® (Stratagene) or pSport1™ plasmid (GIBco/BRL). Ligation of sequences encoding HISAP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of HISAP are needed, e.g. for the production of antibodies, vectors which direct high level expression of HISAP may be used. For example, vectors containing the strong, inducible T5 or T7 bacteriophage promoter may be used.

Yeast expression systems may be used for production of HISAP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of HISAP. Transcription of sequences encoding HISAP may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding HISAP may be ligated into an adenovirus transcription/translation complex consisting of the late promoter and tripartite leader sequence. Insertion in a non-essential E1 or E3 region of the viral genome may be used to obtain infective virus which expresses HISAP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of HISAP in cell lines is preferred. For example, sequences encoding HISAP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate GUS, luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HISAP is inserted within a marker gene sequence, transformed cells containing sequences encoding HISAP can be identified by the absence of marker gene function. Alternatively, a marker gene can be placed in tandem with a sequence encoding HISAP under the control of a single promoter. Expression of the marker gene in response to induction or selection usually indicates expression of the tandem gene as well.

In general, host cells that contain the nucleic acid sequence encoding HISAP and that express HISAP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HISAP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HISAP is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HISAP include oligolabeling, nick translation, end-labeling, or PCR amplification using a labeled nucleotide. Alternatively, the sequences encoding HISAP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HISAP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HISAP may be designed to contain signal sequences which direct secretion of HISAP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding HISAP may be ligated to a heterologous sequence resulting in translation of a fusion protein in any of the aforementioned host systems. For example, a chimeric HISAP protein containing a heterologous moiety that can be recognized by a commercially available antibody may facilitate the screening of peptide libraries for inhibitors of HISAP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HISAP encoding sequence and the heterologous protein sequence, so that HISAP may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled HISAP may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HISAP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (Perkin Elmer). Various fragments of HISAP may be synthesized separately and then combined to produce the full length molecule.

THERAPEUTICS

Chemical and structural homology exists among HISAP and vertebrate immune system associated proteins, particularly immunoglobulins. In addition, HISAP is expressed in cDNA libraries associated with the immune response and cell proliferation. Therefore, HISAP appears to play a role in immune and cell proliferative disorders and infections.

Therefore, in one embodiment, HISAP or a fragment or derivative thereof may be administered to a subject to treat or prevent an immune disorder associated with decreased expression or activity of HISAP. Such disorders can include, but are not limited to, acquired immunodeficiency syndrome (AIDS), X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, immunodeficiency associated with Cushing's disease, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, leukemias such as multiple myeloma, and lymphomas such as Hodgkin's disease.

In another embodiment, a vector capable of expressing HISAP or a fragment or derivative thereof may be administered to a subject to treat or prevent an immune disorder including, but not limited to, those described above.

In a further embodiment, a pharmaceutical composition comprising a substantially purified HISAP in conjunction with a suitable pharmaceutical carrier may be administered to a subject to treat or prevent an immune disorder including, but not limited to, those provided above.

In still another embodiment, an agonist which modulates the activity of HISAP may be administered to a subject to treat or prevent an immune disorder including, but not limited to, those listed above.

In a further embodiment, an antagonist of HISAP may be administered to a subject to treat or prevent an immune disorder associated with increased expression or activity of HISAP including, but not limited to, those discussed above. In one aspect, an antibody which specifically binds HISAP may be used directly as an antagonist or indirectly as a targeting or delivery mechanism for bringing a pharmaceutical agent to cells or tissue which express HISAP.

In an additional embodiment, a vector expressing the complement of the polynucleotide encoding HISAP may be administered to a subject to treat or prevent an immune disorder including, but not limited to, those described above.

In another embodiment, an antagonist of HISAP may be administered to a subject to treat or prevent a cell proliferative disorder. Such disorders may include, but are not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HISAP may be used directly as an antagonist or indirectly as a targeting or delivery mechanism for bringing a pharmaceutical agent to cells or tissue which express HISAP.

In an additional embodiment, a vector expressing the complement of the polynucleotide encoding HISAP may be administered to a subject to treat or prevent a cell proliferative disorder including, but not limited to, those described above.

In another embodiment, HISAP or a fragment or derivative thereof may be administered to a subject to treat or prevent an infection. Such infections can include, but are not limited to, infections by viral agents classified as adenovirus, arenavirus, bunyavirus, calicivirus, coronavirus, filovirus, hepadnavirus, herpesvirus, flavivirus, orthomyxovirus, parvovirus, papovavirus, paramyxovirus, picornavirus, poxvirus, reovirus, retrovirus, rhabdovirus, and togavirus; infections by bacterial agents classified as pneumococcus, staphylococcus, streptococcus, bacillus, corynebacterium, clostridium, meningococcus, gonococcus, listeria, moraxella, kingella, haemophilus, legionella, bordetella, gram-negative enterobacterium including shigella, salmonella, and campylobacter, pseudomonas, vibrio, brucella, francisella, yersinia, bartonella, norcardium, actinomyces, mycobacterium, spirochaetale, rickettsia, chlamydia, and mycoplasma; infections by fungal agents classified as aspergillus, blastomyces, dermatophytes, cryptococcus, coccidioides, malasezzia, histoplasma, and other fungal agents causing various mycoses; and infections by parasites classified as plasmodium or malaria-causing, parasitic entamoeba, leishmania, trypanosoma, toxoplasma, pneumocystis carinii, intestinal protozoa such as giardia, trichomonas, tissue nematodes such as trichinella, intestinal nematodes such as ascaris, lymphatic filarial nematodes, trematodes such as schistosoma, and cestrodes such as tapeworm.

In another embodiment, a vector capable of expressing HISAP or a fragment or derivative thereof may be administered to a subject to treat or prevent an infection including, but not limited to, those described above.

In a further embodiment, a pharmaceutical composition comprising a substantially purified HISAP in conjunction with a suitable pharmaceutical carrier may be administered to a subject to treat or prevent an infection including, but not limited to, those provided above.

In still another embodiment, an agonist which modulates the activity of HISAP may be administered to a subject to treat or prevent an infection including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HISAP may be produced using methods which are generally known in the art. In particular, purified HISAP may be used to produce antibodies or to screen libraries of pharmaceutical agents to identify those which specifically bind HISAP. Antibodies to HISAP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HISAP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HISAP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HISAP amino acids may be fused with those of another protein, such as KLH, and antibodies to the chimeric molecule may be produced.

Monoclonal antibodies to HISAP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495497; Kozbor, D. et al. (1985) J. Immunol. Methods 81:3142; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HISAP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HISAP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HISAP and its specific antibody. A two-site, monoclonal-based immunoassay utilizing monoclonal antibodies reactive to two non-interfering HISAP epitopes is preferred, but a competitive binding assay may also be employed. (Maddox, supra.)

In another embodiment of the invention, the polynucleotides encoding HISAP, or any fragment or complement thereof, may be used for therapeutic purposes. In one aspect, the complement of the polynucleotide encoding HISAP may be used in situations in which it would be desirable to block the transcription of the MRNA. In particular, cells may be transformed with sequences complementary to polynucleotides encoding HISAP. Thus, complementary molecules or fragments may be used to modulate HISAP activity, or to achieve regulation of gene function. Such technology is now well known in the art, and sense or antisense oligonucleotides or larger fragments can be designed from various locations along the coding or control regions of sequences encoding HISAP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HISAP. (See, e.g., Sambrook, supra; and Ausubel, supra.)

Genes encoding HISAP can be turned off by transforming a cell or tissue with expression vectors which express high levels of a polynucleotide, or fragment thereof, encoding HISAP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HISAP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HISAP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HISAP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HISAP, antibodies to HISAP, and mimetics, agonists, antagonists, or inhibitors of HISAP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HISAP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HISAP or fragments thereof, antibodies of HISAP, and agonists, antagonists or inhibitors of HISAP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HISAP may be used for the diagnosis of disorders characterized by expression of HISAP, or in assays to monitor patients being treated with HISAP or agonists, antagonists, or inhibitors of HISAP. Antibodies useful for diagnostic purposes may be prepared in the same manner as described above for therapeutics. Diagnostic assays for HISAP include methods which utilize the antibody and a label to detect HISAP in human body fluids or in extracts of cells or tissues. The antibodies may be used with or without modification, and may be labeled by covalent or noncovalent attachment of a reporter molecule. A wide variety of reporter molecules, several of which are described above, are known in the art and may be used.

A variety of protocols for measuring HISAP, including ELISAs, RIAs, and FACS, are known in the art and provide a basis for diagnosing altered or abnormal levels of HISAP expression. Normal or standard values for HISAP expression are established by combining body fluids or cell extracts taken from normal mammalian subjects, preferably human, with antibody to HISAP under conditions suitable for complex formation. The amount of standard complex formation may be quantitated by various methods, preferably by photometric means. Quantities of HISAP expressed in subject, control, and disease samples from biopsied tissues are compared with the standard values. Deviation between standard and subject values establishes the parameters for diagnosing disease.

In another embodiment of the invention, the polynucleotides encoding HISAP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HISAP may be correlated with disease. The diagnostic assay may be used to determine absence, presence, and excess expression of HISAP, and to monitor regulation of HISAP levels during therapeutic intervention.

In one aspect, hybridization with PCR probes which are capable of detecting polynucleotide sequences, including genomic sequences, encoding HISAP or closely related molecules may be used to identify nucleic acid sequences which encode HISAP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HISAP, alleles, or related sequences.

Probes may also be used for the detection of related sequences, and should preferably have at least 50% sequence identity to any of the HISAP encoding sequences. The hybridization probes of the subject invention may be DNA or RNA and may be derived from a polynucleotide sequence selected from the group consisting of SEQ ID NO:14 through 26 or from genomic sequences including promoters, enhancers, and introns of the HISAP gene.

Means for producing specific hybridization probes for DNAs encoding HISAP include the cloning of polynucleotide sequences encoding HISAP or HISAP derivatives into vectors for the production of MRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$p or $^{35}$S, or by enzymatic labels, such as alkaline phosphatase coupled to the probe via avidin/biotin coupling systems, and the like.

Polynucleotide sequences encoding HISAP may be used for the diagnosis of a disorder associated with expression of HISAP. Examples of such a disorder include, but are not limited to, an immune disorder, such as acquired immunodeficiency syndrome (AIDS), X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, immunodeficiency associated with Cushing's disease, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, leukemias such as multiple myeloma, and lymphomas such as Hodgkin's disease; a cell proliferative disorder such as arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an infection, such as infections by viral agents classified as adenovirus, arenavirus, bunyavirus, calicivirus, coronavirus, filovirus, hepadnavirus, herpesvirus, flavivirus, orthomyxovirus, parvovirus, papovavirus, paramyxovirus, picornavirus, poxvirus, reovirus, retrovirus, rhabdovirus, and togavirus; infections by bacterial agents classified as pneumococcus, staphylococcus, streptococcus, bacillus, corynebacterium, clostridium, meningococcus, gonococcus, listeria, moraxella, kingella, haemophilus, legionella, bordetella, gram-negative enterobacterium including shigella, salmonella, and campylobacter, pseudomonas, vibrio, brucella, francisella, yersinia, bartonella, norcardium, actinomyces, mycobacterium, spirochaetale, rickettsia, chlamydia, and mycoplasma; infections by fungal agents classified as aspergillus, blastomyces, dermatophytes, cryptococcus, coccidioides, malasezzia, histoplasma, and other fungal agents causing various mycoses; and infections by parasites classified as plasmodium or malaria-causing, parasitic entamoeba, leishmania, trypanosoma, toxoplasma, pneumocystis carinii, intestinal protozoa such as giardia, trichomonas, tissue nematodes such as trichinella, intestinal nematodes such as ascaris, lymphatic filarial nematodes, trematodes such as schistosoma, and cestrodes such as tapeworm. The polynucleotide sequences encoding HISAP may be used in Southern or northern analysis, dot blot, or other membrane-based technologies; in PCR technologies; in dipstick, pin, and ELISA assays; and in microarrays utilizing fluids or tissues from patients to detect altered HISAP expression. Such qualitative or quantitative methods are well known in the art.

In a particular aspect, the nucleotide sequences encoding HISAP may be useful in assays that detect the presence of associated disorders, particularly those mentioned above. The nucleotide sequences encoding HISAP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HISAP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HISAP, a normal or standard profile for expression is established. This may be accomplished by combining body fluids or cell extracts taken from normal subjects, either animal or human, with a sequence, or a fragment thereof, encoding HISAP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HISAP may involve the use of PCR. These oligomers may be chemically synthesized, generated enzymatically, or produced in vitro. Oligomers will preferably contain a fragment of a polynucleotide encoding HISAP, or a fragment of a polynucleotide complementary to the polynucleotide encoding HISAP, and will be employed under optimized conditions for identification of a specific gene or condition. Oligomers may also be employed under less stringent conditions for detection or quantitation of closely related DNA or RNA sequences.

Methods which may also be used to quantitate the expression of HISAP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HISAP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) Molecular Biology and Biotechnology, VCH Publishers New York, N.Y., pp. 965–968.) Examples of genetic map data can be found in various scientific journals or at the Online Mendelian Inheritance in Man (OMIM) site. Correlation between the location of the gene encoding HISAP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HISAP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HISAP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HISAP, or fragments thereof, and washed. Bound HISAP is then detected by methods well known in the art. Purified HISAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HISAP specifically compete with a test compound for binding HISAP. In this manner, antibodies can be used to detect the presence of any peptide which shares one or more antigenic determinants with HISAP.

In additional embodiments, the nucleotide sequences which encode HISAP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries cDNA libraries were constructed from frozen tissue obtained from the sources listed below in Table 2. The frozen tissue was homogenized and lysed in guanidinium isothiocyanate solution using a Brinkmann Homogenizer Polytron PT-3000 (Brinkmann Instruments, Westbury, N.J.). The lysate was centrifuged over a CsCl cushion to isolate RNA. Alternatively, RNA was isolated using TRIzol reagent (Catalog #10296-028, Gibco/BRL, Gaithersburg, Md.), a monoplastic solution of phenol and guanidine isothiocyanate. The RNA was extracted with acid phenol, precipitated with sodium acetate and ethanol, resuspended in RNase-free water, and treated with DNase. The RNA was re-extracted with acid phenol and reprecipitated with sodium acetate and ethanol. Poly(A+) RNA was isolated using the Qiagen Oligotex kit (QIAGEN Inc, Chatsworth, Calif.). This procedure may have been modified to accommodate the specific kits, plasmids, reagents, and machinery available at the time of each library's construction.

Poly(A+) RNA was used for cDNA synthesis and construction of the cDNA libraries according to the recommended protocols in the SuperScript plasmid system (Catalog #18248-013, Gibco/BRL). The cDNAs were fractionated on a Sepharose CL4B column (Catalog #275105-01, Pharmacia, Piscataway, N.J.), and those cDNAs exceeding 400 bp were ligated into an appropriate cDNA cloning vector, such as pINCY 1 (Incyte) or pSPORT 1 (Gibco/BRL). The recombinant plasmids were subsequently transformed into DH5α™ competent cells (Catalog #18258-012, Gibco/BRL).

Table 2 lists the tissue sources of each of the cDNA libraries disclosed herein.

TABLE 2

| Protein | Nucleotide | Clone ID | Library | Tissue Source |
|---|---|---|---|---|
| SEQ ID NO:1 | SEQ ID NO:14 | 021145 | ADENINB01 | Adenoid |
| SEQ ID NO:2 | SEQ ID NO:15 | 161752 | ADENINB01 | Adenoid |
| SEQ ID NO:3 | SEQ ID NO:16 | 1320068 | BLADNOT04 | Bladder |
| SEQ ID NO:4 | SEQ ID NO:17 | 1513264 | PANCTUT01 | Pancreatic tumor |
| SEQ ID NO:5 | SEQ ID NO:18 | 1669829 | BMARNOT03 | Bone marrow |
| SEQ ID NO:6 | SEQ ID NO:19 | 2280869 | COLSUCT01 | Sigmoid colon |
| SEQ ID NO:7 | SEQ ID NO:20 | 2492122 | ADRETUT05 | Adrenal tumor |
| SEQ ID NO:8 | SEQ ID NO:21 | 2747531 | LUNGTUT11 | Lung tumor |
| SEQ ID NO:9 | SEQ ID NO:22 | 2784232 | BRSTNOT13 | Breast |
| SEQ ID NO:10 | SEQ ID NO:23 | 2872705 | THYRNOT10 | Thyroid |
| SEQ ID NO:11 | SEQ ID NO:24 | 3056213 | LNODNOT08 | Lymph node |
| SEQ ID NO:12 | SEQ ID NO:25 | 3116314 | LUNGTUT13 | Lung tumor |
| SEQ ID NO:13 | SEQ ID NO:26 | 3551457 | SYNONOT01 | Synovium |

II Isolation and Sequencing of cDNA Clones

Plasmid DNA was released from the cells and purified using the REAL Prep 96 Plasmid Kit (Catalog #26173, QIAGEN Inc). The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. And Henikoff G. J., Nucleic Acids Research (1991) 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HISAP occurs. Abundance and percent abundance are also reported. Abundance directly reflects the number of times a particular transcript is represented in a cDNA library, and percent abundance is abundance divided by the total number of sequences examined in the cDNA library.

V. Extension of HISAP Encoding Polynucleotides

The nucleic acid sequences of Incyte Clones 021145, 161752, 1320068, 1513264, 1669829, 2280869, 2492122, 2747531, 2784232, 2872705, 3056213, 3116314, and 3551457 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |

-continued

| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 μl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 40° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:14 through 26 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:14 through 26 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HISAP-encoding sequences, or any parts thereof, are used to detect, decrease, or inhibit expression of naturally occurring HISAP. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HISAP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HISAP-encoding transcript.

IX. Expression of HISAP

Expression and purification of HISAP is achieved using bacterial or virus-based expression systems. For expression of HISAP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HISAP upon induction with isopropyl beta-D-thiogalactopyranoside (IPTG). Expression of HISAP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HISAP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, HISAP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from HISAP at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified HISAP obtained by these methods can be used directly in the following activity assay.

X. Demonstration of HISAP Activity

HISAP activity is exemplified by that of immunoglobulins, which recognize and precipitate antigens from serum. The quantitative precipitin reaction measures this activity. (Golub, E. S. et al. (1987) *Immunology: A Synthesis*, Sinauer Associates, Sunderland, Mass., pages 113–115.) HISAP is isotopically labeled using methods known in the art. Various serum concentrations are added to constant amounts of labeled HISAP. HISAP-antigen complexes precipitate out of solution and are collected by centrifugation. The amount of precipitable HISAP-antigen complex is proportional to the amount of radioisotope detected in the precipitate. The amount of precipitable HISAP-antigen complex is plotted against the serum concentration. For various serum concentrations, a characteristic precipitin curve is obtained, in which the amount of precipitable HISAP-antigen complex initially increases proportionately with increasing serum concentration, peaks at the equivalence point, and then decreases proportionately with further increases in serum concentration. Thus, the amount of precipitable HISAP-antigen complex is a measure of HISAP activity which is characterized by sensitivity to both limiting and excess quantities of antigen.

XI. Functional Assays

HISAP function is assessed by expressing the sequences encoding HISAP at physiologically elevated levels in mammalian cell culture systems. cDNA is subcloned into a mammalian expression vector containing a strong promoter that drives high levels of cDNA expression. Vectors of choice include pCMV.Sport™ (Life Technologies™, Gaithersburg, Md.) and pCR™ 3.1 (Invitrogen™, Carlsbad, Calif., both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP and to evaluate properties such as their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; downregulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of HISAP on gene expression can be assessed using highly purified populations of cells transfected with sequences encoding HISAP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding HISAP and other genes of interest can be analyzed by Northern analysis or microarray techniques.

XII. Production of HISAP Specific Antibodies

HISAP substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the HISAP amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XIII. Purification of Naturally Occurring HISAP Using Specific Antibodies

Naturally occurring or recombinant HISAP is substantially purified by immunoaffinity chromatography using antibodies specific for HISAP. An immunoaffinity column is constructed by covalently coupling anti-HISAP antibody to an activated chromatographic resin, such as CNBr-activated Sepharose (Pharmacia & Upjohn). After the coupling, the resin is blocked and washed according to the manufacturer's instructions.

Media containing HISAP are passed over the immunoaffinity column, and the column is washed under conditions that allow the preferential absorbance of HISAP (e.g., high ionic strength buffers in the presence of detergent). The column is eluted under conditions that disrupt antibody/HISAP binding (e.g., a buffer of pH 2 to pH 3, or a high concentration of a chaotrope, such as urea or thiocyanate ion), and HISAP is collected.

XIV. Identification of Molecules Which Interact with HISAP

HISAP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HISAP, washed, and any wells with labeled HISAP complex are assayed. Data obtained using different concentrations of HISAP are used to calculate values for the number, affinity, and association of HISAP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide selected from the group consisting of SEQ ID NO:1, SEQ ID NO:2, SEQ ID NO:4, SEQ ID NO:5, SEQ ID NO:6, SEQ ID NO:7, SEQ ID NO:8. SEQ ID NO:9, SEQ ID NO:10, SEQ ID NO:11, SEQ ID NO:12, and SEQ ID NO:13.

2. An isolated and purified polynucleotide comprising a sequence which is completely complementary to the polynucleotide sequence of claim 1.

3. An isolated and purified polynucleotide comprising a polynucleotide sequence selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26.

4. An isolated and purified polynucleotide comprising a sequence which is completely complementary to the polynucleotide sequence of claim 3. SEQ ID NO:26.

5. An expression vector containing the polynucleotide of claim 1.

6. A host cell containing the expression vector of claim 5.

7. A method for producing a polypeptide, the method comprising the steps of:
   a) culturing the host cell of claim 6 under conditions suitable for the expression of the polypeptide; and
   b) recovering the polypeptide from the host cell culture.

8. A method for detecting a polynucleotide, the method comprising the steps of:
   (a) hybridizing the polynucleotide of claim 2 to at least one of the nucleic acids in a sample, thereby forming a hybridization complex; and
   (b) detecting the hybridization complex, wherein the presence of the hybridization complex correlates with the presence of the polynucleotide in the sample.

9. The method of claim 8 wherein the nucleic acids of the biological sample are amplified by the polymerase chain reaction prior to the hybridization step.

10. An isolated and purified fragment of the polynucleotide of claim 3 selected from the group consisting of nucleotide 402 to nucleotide 443 of SEQ ID NO:14, nucleotide 432 to nucleotide 467 of SEQ ID NO:17, nucleotide 418 to nucleotide 453 of SEQ ID NO:18, nucleotide 346 to nucleotide 366 of SEQ ID NO:19, nucleotide 278 to nucleotide 298 of SEQ ID NO:20, nucleotide 251 to nucleotide 283 of SEQ ID NO:21, nucleotide 358 to nucleotide 387 of SEQ ID NO:23, nucleotide 396 to nucleotide 419 of SEQ ID NO:24, nucleotide 163 to nucleotide 225 of SEQ ID NO:25, and nucleotide 389 to nucleotide 412 of SEQ ID NO:26.

11. An isolated and purified polynucleotide comprising a sequence which is completely complementary to the polynucleotide of claim 10.

12. A method for detecting a polynucleotide, the method comprising the steps of:
 (a) hybridizing the polynucleotide of claim 11 to at least one nucleic acid in a sample, thereby forming a hybridization complex; and
 (b) detecting the hybridization complex, wherein the presence of the hybridization complex correlates with the presence of the polynucleotide in the sample.

13. The method of claim 12 further comprising amplifying the polynucleotide prior to hybridization.

14. An isolated and purified fragment of a polynucleotide selected from the group consisting of nucleotide 124 to nucleotide 150 of SEQ ID NO:15 and nucleotide 102 to nucleotide 128 of SEQ ID NO:16.

15. An isolated and purified fragment of a polynucleotide consisting of a sequence which is completely complementary to the polynucleotide of claim 14.

16. A method for detecting a polynucleotide, the method comprising the steps of:
 (a) hybridizing the polynucleotide of claim 15 to at least one nucleic acid in a sample, thereby forming a hybridization complex; and
 (b) detecting the hybridization complex, wherein the presence of the hybridization complex correlates with the presence of the polynucleotide in the sample.

17. The method of claim 16 further comprising amplifying the polynucleotide prior to hybridization.

* * * * *

UNITED STATES PATENT AND TRADEMARK OFFICE
CERTIFICATE OF CORRECTION

PATENT NO. : 6,135,941
DATED : Oct. 24, 2000
INVENTOR(S) : Jennifer L. Hillman, Y. Tom Tang, Henry Yue, Janice Au-Young, Neil C. Corley, Karl J. Guegler, Mariah R. Baughn It is certified that error appears in the above-identified patent and that said Letters Patent are hereby corrected as shown below:

Col. 95, line 65, delete "3. SEQ ID NO: 26.".

Signed and Sealed this

Eighth Day of May, 2001

Attest:

NICHOLAS P. GODICI

Attesting Officer    Acting Director of the United States Patent and Trademark Office

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
        (A) LENGTH: 499 amino acids
        (B) TYPE: amino acid
        (C) STRANDEDNESS: single
        (D) TOPOLOGY: linear (vii) IMMEDIATE SOURCE:
        (A) LIBRARY: ADENINB01
        (B) CLONE: 021145

(xi) SEQUENCE DESCRIPTION: SEQ ID NO:1:

```
Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Ile
            20                  25                  30

Pro Thr Glu Thr Leu Thr Leu Thr Cys Thr Phe Ser Gly Phe Ser Leu
                35                  40                  45

Ser Thr Ser Gly Val Gly Val Gly Trp Ile Arg Gln Pro Pro Gly Lys
        50                  55                  60

Ala Leu Glu Trp Leu Ala Leu Ile Tyr Trp Asp Asp Lys Arg Asn
65                  70                  75                  80

Ser Pro Ser Leu Lys Ser Arg Leu Thr Ile Thr Lys Asp Thr Ser Lys
                85                  90                  95
```

```
Asn Gln Val Val Leu Thr Met Thr Asn Met Asp Pro Glu Asp Thr Ala
            100                 105                 110
Thr Tyr Tyr Cys Ala His Arg Gln Gly Tyr Cys Ser Ser Thr Ser Cys
            115                 120                 125
Tyr Tyr Gln Trp Phe Asp Pro Trp Gly Gln Gly Thr Gln Val Thr Val
            130                 135                 140
Ser Ser Ala Ser Pro Thr Ser Pro Lys Val Phe Pro Leu Ser Leu Cys
145                 150                 155                 160
Ser Thr Gln Pro Asp Gly Asn Val Val Ile Ala Cys Leu Val Gln Gly
                165                 170                 175
Phe Phe Pro Gln Glu Pro Leu Ser Val Thr Trp Ser Glu Ser Gly Gln
                180                 185                 190
Gly Val Thr Ala Arg Asn Phe Pro Pro Ser Gln Asp Ala Ser Gly Asp
                195                 200                 205
Leu Tyr Thr Thr Ser Ser Gln Leu Thr Leu Pro Ala Thr Gln Cys Leu
            210                 215                 220
Ala Gly Lys Ser Val Thr Cys His Val Lys His Tyr Thr Asn Pro Ser
225                 230                 235                 240
Gln Asp Val Thr Val Pro Cys Pro Val Pro Ser Thr Pro Pro Thr Pro
                245                 250                 255
Ser Pro Ser Thr Pro Pro Thr Pro Ser Pro Ser Cys Cys His Pro Arg
                260                 265                 270
Leu Ser Leu His Arg Pro Ala Leu Glu Asp Leu Leu Leu Gly Ser Glu
            275                 280                 285
Ala Asn Leu Thr Cys Thr Leu Thr Gly Leu Arg Asp Ala Ser Gly Val
            290                 295                 300
Thr Phe Thr Trp Thr Pro Ser Ser Gly Lys Ser Ala Val Gln Gly Pro
305                 310                 315                 320
Pro Glu Arg Asp Leu Cys Gly Cys Tyr Ser Val Ser Ser Val Leu Pro
                325                 330                 335
Gly Cys Ala Gln Pro Trp Asn His Gly Glu Thr Phe Thr Cys Thr Ala
                340                 345                 350
Ala His Pro Glu Leu Lys Thr Pro Leu Thr Ala Asn Ile Thr Lys Ser
            355                 360                 365
Gly Asn Thr Phe Arg Pro Glu Val His Leu Leu Pro Pro Pro Ser Glu
            370                 375                 380
Glu Leu Ala Leu Asn Glu Leu Val Thr Leu Thr Cys Leu Ala Arg Gly
385                 390                 395                 400
Phe Ser Pro Lys Asp Val Leu Val Arg Trp Leu Gln Gly Ser Gln Glu
                405                 410                 415
Leu Pro Arg Glu Lys Tyr Leu Thr Trp Ala Ser Arg Gln Glu Pro Ser
            420                 425                 430
Gln Gly Thr Thr Thr Phe Ala Val Thr Ser Ile Leu Arg Val Ala Ala
            435                 440                 445
Glu Asp Trp Lys Lys Gly Asp Thr Phe Ser Cys Met Val Gly His Glu
            450                 455                 460
Ala Leu Pro Leu Ala Phe Thr Gln Lys Thr Ile Asp Arg Leu Ala Gly
465                 470                 475                 480
Lys Pro Thr His Val Asn Val Ser Val Val Met Ala Glu Val Asp Gly
                485                 490                 495
Thr Cys Tyr (2) INFORMATION FOR SEQ ID NO:2:
```

(i) SEQUENCE CHARACTERISTICS:
    (A) LENGTH: 234 amino acids
    (B) TYPE: amino acid
    (C) STRANDEDNESS: single
    (D) TOPOLOGY: linear (vii) IMMEDIATE SOURCE:
    (A) LIBRARY: ADENINB01
    (B) CLONE: 161752

(xi) SEQUENCE DESCRIPTION: SEQ ID NO:2:

Met Gly Ser Gln Val His Leu Leu Ser Phe Leu Leu Leu Trp Ile Ser
 1               5                  10                  15

Asp Thr Arg Ala Glu Thr Thr Leu Thr Gln Ser Pro Val Phe Met Ser
            20                  25                  30

Ala Thr Pro Gly Asp Lys Val Asn Ile Ser Cys Lys Ala Ser Gln Asp
        35                  40                  45

Ile Asp Asp Asp Met Asn Trp Tyr Gln Gln Lys Pro Gly Glu Val Val
 50                  55                  60

Ile Phe Ile Ile Gln Glu Ala Thr Thr Leu Val Pro Gly Phe Ser Pro
 65                  70                  75                  80

Arg Phe Ser Gly Ser Gly Tyr Gly Thr Asp Phe Thr Leu Thr Ile Asn
                85                  90                  95

Asn Ile Gln Ser Glu Asp Ser Ala Tyr Tyr Phe Cys Leu Gln His Asp
            100                 105                 110

Asn Phe Pro Val Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

(2) INFORMATION FOR SEQ ID NO:3:

(i) SEQUENCE CHARACTERISTICS:
    (A) LENGTH: 150 amino acids
    (B) TYPE: amino acid
    (C) STRANDEDNESS: single
    (D) TOPOLOGY: linear (vii) IMMEDIATE SOURCE:
    (A) LIBRARY: BLADNOT04
    (B) CLONE: 1320068

(xi) SEQUENCE DESCRIPTION: SEQ ID NO:3:

Met Ser Gly Glu Leu Ser Asn Arg Phe Gln Gly Gly Lys Ala Phe Gly
 1               5                  10                  15

Leu Leu Lys Ala Arg Gln Glu Arg Leu Ala Glu Ile Asn Arg Glu
            20                  25                  30

```
Phe Leu Cys Asp Gln Lys Tyr Ser Asp Glu Glu Asn Leu Pro Glu Lys
             35                  40                  45

Leu Thr Ala Phe Lys Glu Lys Tyr Met Glu Phe Asp Leu Asn Asn Glu
 50                  55                  60

Gly Glu Ile Asp Leu Met Ser Leu Lys Arg Met Met Glu Lys Leu Gly
 65                  70                  75                  80

Val Pro Lys Thr His Leu Glu Met Lys Lys Met Ile Ser Glu Val Thr
                 85                  90                  95

Gly Gly Val Ser Asp Thr Ile Ser Tyr Arg Asp Phe Val Asn Met Met
                100                 105                 110

Leu Gly Lys Arg Ser Ala Val Leu Lys Leu Val Met Met Phe Glu Gly
             115                 120                 125

Lys Ala Asn Glu Ser Ser Pro Lys Pro Val Gly Pro Pro Glu Arg
 130                 135                 140

Asp Ile Ala Ser Leu Pro
 145                 150

(2) INFORMATION FOR SEQ ID NO:4:

(i) SEQUENCE CHARACTERISTICS:
        (A) LENGTH: 473 amino acids
        (B) TYPE: amino acid
        (C) STRANDEDNESS: single
        (D) TOPOLOGY: linear (vii) IMMEDIATE SOURCE:
        (A) LIBRARY: PANCTUT01
        (B) CLONE: 1513264

(xi) SEQUENCE DESCRIPTION: SEQ ID NO:4:

Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                 20                  25                  30

Pro Ser Glu Thr Leu Ser Leu Thr Cys Ala Val Ser Gly Gly Ser Ile
             35                  40                  45

Thr Ser Gly Gly Tyr Tyr Trp Ser Trp Ile Arg Gln Pro Pro Gly Lys
 50                  55                  60

Gly Leu Glu Trp Ile Gly Tyr Ile Tyr Tyr Ser Gly Ser Thr Leu Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
                100                 105                 110

Val Tyr Tyr Cys Ala Arg Asp Asp Val Gly Leu Arg Gly Gly Asn Tyr
             115                 120                 125

Gly Met Asp Val Trp Gly Gln Gly Thr Leu Val Thr Val Ser Ser Ala
 130                 135                 140

Ser Thr Lys Gly Pro Ser Val Phe Pro Leu Ala Pro Ser Ser Lys Ser
 145                 150                 155                 160

Thr Ser Gly Gly Thr Ala Ala Leu Gly Cys Leu Val Lys Asp Tyr Phe
                 165                 170                 175

Pro Glu Pro Val Thr Val Ser Trp Asn Ser Gly Ala Leu Thr Ser Gly
                 180                 185                 190

Val His Thr Phe Pro Ala Val Leu Gln Ser Ser Gly Leu Tyr Ser Leu
             195                 200                 205

Ser Ser Val Val Thr Val Pro Ser Ser Ser Leu Gly Thr Gln Thr Tyr
```

-continued

```
            210                 215                 220
Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
                275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
                450                 455                 460

Lys Ser Leu Ser Leu Ser Pro Gly Lys
465                 470
```

(2) INFORMATION FOR SEQ ID NO:5:

(i) SEQUENCE CHARACTERISTICS:
        (A) LENGTH: 483 amino acids
        (B) TYPE: amino acid
        (C) STRANDEDNESS: single
        (D) TOPOLOGY: linear (vii) IMMEDIATE SOURCE:
        (A) LIBRARY: BMARNOT03
        (B) CLONE: 1669829

(xi) SEQUENCE DESCRIPTION: SEQ ID NO:5:

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
                35                  40                  45

Asp Asp His Ala Met His Trp Val Arg Gln Ile Pro Gly Lys Gly Leu
                50                  55                  60

Glu Trp Val Ser Gly Ile Asn Trp His Ser Val Thr Ile Gly Tyr Ala
65                  70                  75                  80
```

-continued

```
Asn Ser Val Lys Gly Arg Phe Thr Ile Ser Arg Asp Asn Ala Lys Ser
             85                  90                  95

Ser Leu Tyr Leu Gln Met Asn Ser Leu Arg Val Glu Asp Thr Ala Leu
        100                 105                 110

Asn Asn Trp Ala Lys Asp Leu Lys Thr Pro Arg Gly Gly Tyr Ser Ala
            115                 120                 125

Ser Met Asp Tyr Trp Gly Gln Gly Thr Leu Val Ile Val Ser Ser Ala
        130                 135                 140

Ser Pro Thr Ser Pro Lys Val Phe Pro Leu Ser Leu Asp Ser Thr Pro
145                 150                 155                 160

Gln Asp Gly Asn Val Val Ala Cys Leu Val Gln Gly Phe Phe Pro
                165                 170                 175

Gln Glu Pro Leu Ser Val Thr Trp Ser Glu Ser Gly Gln Asn Val Thr
            180                 185                 190

Ala Arg Asn Phe Pro Pro Ser Gln Asp Ala Ser Gly Asp Leu Tyr Thr
            195                 200                 205

Thr Ser Ser Gln Leu Thr Leu Pro Ala Thr Gln Cys Pro Asp Gly Lys
        210                 215                 220

Ser Val Thr Cys His Val Lys His Tyr Thr Asn Pro Ser Gln Asp Val
225                 230                 235                 240

Thr Val Pro Cys Pro Val Pro Pro Pro Pro Cys Cys His Pro Arg
                245                 250                 255

Leu Ser Leu His Arg Pro Ala Leu Glu Asp Leu Leu Leu Gly Ser Glu
            260                 265                 270

Ala Asn Leu Thr Cys Thr Leu Thr Gly Leu Arg Asp Ala Ser Gly Ala
        275                 280                 285

Thr Phe Thr Trp Thr Pro Ser Ser Gly Lys Ser Ala Val Gln Gly Pro
        290                 295                 300

Pro Glu Arg Asp Leu Cys Gly Cys Tyr Ser Val Ser Ser Val Leu Pro
305                 310                 315                 320

Gly Cys Ala Gln Pro Trp Asn His Gly Glu Thr Phe Thr Cys Thr Ala
                325                 330                 335

Ala His Pro Glu Leu Lys Thr Pro Leu Thr Ala Asn Ile Thr Lys Ser
            340                 345                 350

Gly Asn Thr Phe Arg Pro Glu Val His Leu Leu Pro Pro Pro Ser Glu
        355                 360                 365

Glu Leu Ala Leu Asn Glu Leu Val Thr Leu Thr Cys Leu Ala Arg Gly
        370                 375                 380

Phe Ser Pro Lys Asp Val Leu Val Arg Trp Leu Gln Gly Ser Gln Glu
385                 390                 395                 400

Leu Pro Arg Glu Lys Tyr Leu Thr Trp Ala Ser Arg Gln Glu Pro Ser
            405                 410                 415

Gln Gly Thr Thr Thr Phe Ala Val Thr Ser Ile Leu Arg Val Ala Ala
            420                 425                 430

Glu Asp Trp Lys Lys Gly Asp Thr Phe Ser Cys Met Val Gly His Glu
        435                 440                 445

Ala Leu Pro Leu Ala Phe Thr Gln Lys Thr Ile Asp Arg Leu Ala Gly
        450                 455                 460

Lys Pro Thr His Val Asn Val Ser Val Val Met Ala Glu Val Asp Gly
465                 470                 475                 480

Thr Cys Tyr
```

(2) INFORMATION FOR SEQ ID NO:6:

(i) SEQUENCE CHARACTERISTICS:
        (A) LENGTH: 234 amino acids
        (B) TYPE: amino acid
        (C) STRANDEDNESS: single
        (D) TOPOLOGY: linear (vii) IMMEDIATE SOURCE:
        (A) LIBRARY: COLSUCT01
        (B) CLONE: 2280869

(xi) SEQUENCE DESCRIPTION: SEQ ID NO:6:

```
Met Glu Ala Pro Ala Gln Leu Leu Phe Leu Leu Leu Trp Leu Pro
 1               5                  10                  15

Asp Ser Phe Gly Glu Ile Val Met Thr Gln Ser Pro Ala Ile Val Ser
                20                  25                  30

Leu Ser Pro Gly Glu Arg Ala Thr Leu Ser Cys Arg Ala Ser Gln Ser
            35                  40                  45

Ile Gly Ser Thr Ile Ala Trp Tyr Gln Gln Arg Pro Gly Gln Ser Pro
        50                  55                  60

Arg Leu Leu Ile Tyr Gly Ala Ser Thr Arg Ala Thr Gly Val Pro Pro
 65                  70                  75                  80

Arg Phe Ser Gly Gly Gly Ser Gly Thr Glu Phe Thr Leu Phe Ile Ser
                85                  90                  95

Ser Leu Gln Ser Glu Asp Phe Ala Leu Tyr Tyr Cys Gln Gln Tyr Lys
            100                 105                 110

Gly Trp Pro Leu Thr Phe Gly Gly Gly Thr Arg Val Gln Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

(2) INFORMATION FOR SEQ ID NO:7:

(i) SEQUENCE CHARACTERISTICS:
        (A) LENGTH: 236 amino acids
        (B) TYPE: amino acid
        (C) STRANDEDNESS: single
        (D) TOPOLOGY: linear (vii) IMMEDIATE SOURCE:
        (A) LIBRARY: ADRETUT05
        (B) CLONE: 2492122

(xi) SEQUENCE DESCRIPTION: SEQ ID NO:7:

```
Met Ala Trp Ser Pro Leu Leu Leu Thr Leu Leu Ala His Cys Thr Gly
 1               5                  10                  15

Ser Trp Ala Gln Ser Val Leu Thr Gln Pro Pro Ser Val Ser Gly Ala
                20                  25                  30
```

```
Pro Gly Gln Arg Val Thr Ile Ser Cys Thr Gly Ser Ser Ser Asn Ile
            35                  40                  45
Gly Ala Gly Tyr Asp Val His Trp Tyr Gln Gln Leu Pro Gly Thr Ala
 50                      55                  60
Pro Lys Leu Leu Ile Tyr Gly Ser Arg Asn Arg Pro Ser Gly Val Pro
 65                  70                  75                  80
Asp Arg Phe Ser Gly Ser Lys Ser Gly Thr Ser Ala Ser Leu Ala Ile
                 85                  90                  95
Thr Gly Leu Gln Ala Glu Asp Glu Ala Asp Tyr Tyr Cys Gln Ser Tyr
                100                 105                 110
Asp Ser Ser Leu Ser Gly Val Val Phe Gly Gly Gly Thr Lys Leu Thr
            115                 120                 125
Val Leu Gly Gln Pro Lys Ala Ala Pro Ser Val Thr Leu Phe Pro Pro
130                 135                 140
Ser Ser Glu Glu Leu Gln Ala Asn Arg Ala Thr Leu Val Cys Leu Ile
145                 150                 155                 160
Ser Asp Phe Tyr Pro Gly Ala Val Thr Val Ala Trp Lys Ala Asp Ser
                165                 170                 175
Ser Pro Val Lys Ala Gly Val Glu Thr Thr Thr Pro Ser Lys Gln Ser
            180                 185                 190
Asn Asn Lys Tyr Ala Ala Ser Ser Tyr Leu Ser Leu Thr Pro Glu Gln
            195                 200                 205
Trp Lys Ser His Arg Ser Tyr Ser Cys Gln Val Thr His Glu Gly Ser
            210                 215                 220
Thr Val Glu Lys Thr Val Ala Pro Thr Glu Cys Ser
225                 230                 235

(2) INFORMATION FOR SEQ ID NO:8:

(i) SEQUENCE CHARACTERISTICS:
        (A) LENGTH: 467 amino acids
        (B) TYPE: amino acid
        (C) STRANDEDNESS: single
        (D) TOPOLOGY: linear (vii) IMMEDIATE SOURCE:
        (A) LIBRARY: LUNGTUT11
        (B) CLONE: 2747531

(xi) SEQUENCE DESCRIPTION: SEQ ID NO:8:

Met Asp Cys Thr Trp Arg Ile Leu Phe Leu Val Ala Ala Ala Thr Gly
 1               5                  10                  15
Thr His Ala Gln Val Gln Leu Val Gln Ser Gly Ala Glu Val Lys Lys
             20                  25                  30
Pro Gly Ala Ser Val Gln Val Ser Cys Thr Val Ser Gly Phe Thr Leu
            35                  40                  45
Ser Asp Leu Ser Val His Trp Val Arg Gln Ala Pro Gly Gln Gly Leu
 50                  55                  60
Glu Trp Met Gly Leu Ala Pro Glu Asn Gly Glu Ala Val Tyr Ala
 65                  70                  75                  80
Gln Lys Phe Leu Gly Arg Leu Thr Leu Ser Glu Asp Thr Ser Ala Asp
                 85                  90                  95
Thr Ala Tyr Met Phe Leu Asn Asn Leu Gly Ser Glu Asp Ser Ala Ile
                100                 105                 110
Tyr Tyr Cys Ala Arg Gln His Tyr Asp Phe Phe Asp Phe Trp Gly
            115                 120                 125
```

```
Gln Gly Thr Met Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

(2) INFORMATION FOR SEQ ID NO:9:

(i) SEQUENCE CHARACTERISTICS:
        (A) LENGTH: 307 amino acids
        (B) TYPE: amino acid
        (C) STRANDEDNESS: single
        (D) TOPOLOGY: linear (vii) IMMEDIATE SOURCE:
        (A) LIBRARY: BRSTNOT13
        (B) CLONE: 2784232
```

-continued (xi) SEQUENCE DESCRIPTION: SEQ ID NO:9:

```
Met Gly Gly Phe Gln Arg Gly Lys Tyr Gly Thr Met Ala Glu Gly Arg
 1               5                  10                  15

Ser Glu Asp Asn Leu Ser Ala Thr Pro Pro Ala Leu Arg Ile Ile Leu
            20                  25                  30

Val Gly Lys Thr Gly Cys Gly Lys Ser Ala Thr Gly Asn Ser Ile Leu
        35                  40                  45

Gly Gln Pro Val Phe Glu Ser Lys Leu Arg Ala Gln Ser Val Thr Arg
    50                  55                  60

Thr Cys Gln Val Lys Thr Gly Thr Trp Asn Arg Lys Val Leu Val
65                  70                  75                  80

Val Asp Thr Pro Ser Ile Phe Glu Ser Gln Ala Asp Thr Gln Glu Leu
            85                  90                  95

Tyr Lys Asn Ile Gly Asp Cys Tyr Leu Leu Ser Ala Pro Gly Pro His
            100                 105                 110

Val Leu Leu Leu Val Ile Gln Leu Gly Arg Phe Thr Ala Gln Asp Thr
            115                 120                 125

Val Ala Ile Arg Lys Val Lys Glu Val Phe Gly Thr Gly Ala Met Arg
    130                 135                 140

His Val Val Ile Leu Phe Thr His Lys Glu Asp Leu Gly Gly Gln Ala
145                 150                 155                 160

Leu Asp Asp Tyr Val Ala Asn Thr Asp Asn Cys Ser Leu Lys Asp Leu
                165                 170                 175

Val Arg Glu Cys Glu Arg Arg Tyr Cys Ala Phe Asn Asn Trp Gly Ser
            180                 185                 190

Val Glu Glu Gln Arg Gln Gln Gln Ala Glu Leu Leu Ala Val Ile Glu
        195                 200                 205

Arg Leu Gly Arg Glu Arg Glu Gly Ser Phe His Ser Asn Asp Leu Phe
    210                 215                 220

Leu Asp Ala Gln Leu Leu Gln Arg Thr Gly Ala Gly Ala Cys Gln Glu
225                 230                 235                 240

Asp Tyr Arg Gln Tyr Gln Ala Lys Val Glu Trp Gln Val Glu Lys His
                245                 250                 255

Lys Gln Glu Leu Arg Glu Asn Glu Ser Asn Trp Ala Tyr Lys Ala Leu
            260                 265                 270

Leu Arg Val Lys His Leu Met Leu Leu His Tyr Glu Ile Phe Val Phe
        275                 280                 285

Leu Leu Leu Cys Ser Ile Leu Phe Phe Ile Ile Phe Leu Phe Ile Phe
    290                 295                 300

His Tyr Ile
305
```

(2) INFORMATION FOR SEQ ID NO:10:

(i) SEQUENCE CHARACTERISTICS:
        (A) LENGTH: 235 amino acids
        (B) TYPE: amino acid
        (C) STRANDEDNESS: single
        (D) TOPOLOGY: linear (vii) IMMEDIATE SOURCE:
        (A) LIBRARY: THYRNOT10
        (B) CLONE: 2872705

(xi) SEQUENCE DESCRIPTION: SEQ ID NO:10:

```
Met Ala Trp Ala Leu Leu Phe Leu Thr Leu Leu Thr Gln Gly Thr Gly
 1               5                  10                  15
```

```
Ser Trp Ala Gln Ser Ala Leu Thr Gln Pro Ala Ser Val Ser Gly Ser
             20                  25                  30

Pro Gly Gln Ser Ile Thr Ile Ser Cys Thr Gly Thr Ser Ser Asp Val
             35                  40                  45

Gly Gly Tyr Asn Tyr Val Ser Trp Tyr Gln Gln Ser Pro Gly Thr Ala
         50                  55                  60

Pro Lys Leu Met Ile Tyr Glu Val Ser Asn Arg Pro Ser Gly Val Ser
 65                  70                  75                  80

Asn Arg Phe Ser Gly Ser Lys Ser Gly Asn Thr Ala Ser Leu Thr Ile
                 85                  90                  95

Ser Gly Leu Gln Ala Glu Asp Glu Ala Asp Tyr Tyr Cys Ser Ser Tyr
                100                 105                 110

Val Gly Asn Asn Ile Val Val Phe Gly Gly Gly Thr Lys Leu Thr Val
                115                 120                 125

Leu Gly Gln Pro Lys Ala Ala Pro Ser Val Thr Leu Phe Pro Pro Ser
            130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Asn Lys Tyr Ala Ala Ser Ser Tyr Leu Ser Leu Thr Pro Glu Gln Trp
                195                 200                 205

Lys Ser His Arg Ser Tyr Ser Cys Gln Val Thr His Glu Gly Ser Thr
            210                 215                 220

Val Glu Lys Thr Val Ala Pro Thr Glu Cys Ser
225                 230                 235

(2) INFORMATION FOR SEQ ID NO:11:

(i) SEQUENCE CHARACTERISTICS:
        (A) LENGTH: 240 amino acids
        (B) TYPE: amino acid
        (C) STRANDEDNESS: single
        (D) TOPOLOGY: linear (vii) IMMEDIATE SOURCE:
        (A) LIBRARY: LNODNOT08
        (B) CLONE: 3056213

(xi) SEQUENCE DESCRIPTION: SEQ ID NO:11:

Met Ser Val Pro Thr Met Ala Trp Met Met Leu Leu Leu Gly Leu Leu
 1               5                  10                  15

Ala Tyr Gly Ser Gly Val Asp Ser Gln Thr Val Val Thr Gln Glu Pro
             20                  25                  30

Ser Phe Ser Val Ser Pro Gly Gly Thr Val Thr Leu Thr Cys Gly Leu
             35                  40                  45

Ser Ser Gly Ser Val Ser Thr Ser Asn Tyr Pro Ser Trp Tyr Gln Gln
         50                  55                  60

Thr Pro Gly Gln Ala Pro Arg Thr Leu Ile Tyr Gly Thr Ser Val Arg
 65                  70                  75                  80

Ser Ser Gly Val Pro Asp Arg Phe Ser Gly Ser Ile Leu Gly Asn Lys
                 85                  90                  95

Ala Gly Leu Thr Ile Thr Gly Ala Gln Ala Asp Asp Glu Ser Asp Tyr
                100                 105                 110
```

```
Tyr Cys Val Leu Tyr Arg Arg Ser Gly Ser Trp Val Phe Gly Gly Gly
            115                 120                 125

Thr Lys Leu Ser Val Leu Gly Gln Pro Lys Ala Ala Pro Ser Val Thr
130             135                 140

Leu Phe Pro Pro Ser Ser Glu Glu Leu Gln Ala Asn Lys Ala Thr Leu
145                 150                 155                 160

Val Cys Leu Ile Ser Asp Phe Tyr Pro Gly Ala Val Thr Val Ala Trp
                165                 170                 175

Lys Ala Asp Ser Ser Pro Val Lys Ala Gly Val Glu Thr Thr Thr Pro
                180                 185                 190

Ser Lys Gln Ser Asn Asn Lys Tyr Ala Ala Ser Ser Tyr Leu Ser Leu
            195                 200                 205

Thr Pro Glu Gln Trp Lys Ser His Lys Ser Tyr Ser Cys Gln Val Thr
            210                 215                 220

His Glu Gly Ser Thr Val Glu Lys Thr Val Ala Pro Thr Glu Cys Ser
225                 230                 235                 240

(2) INFORMATION FOR SEQ ID NO:12:

(i) SEQUENCE CHARACTERISTICS:
        (A) LENGTH: 235 amino acids
        (B) TYPE: amino acid
        (C) STRANDEDNESS: single
        (D) TOPOLOGY: linear (vii) IMMEDIATE SOURCE:
        (A) LIBRARY: LUNGTUT13
        (B) CLONE: 3116314

(xi) SEQUENCE DESCRIPTION: SEQ ID NO:12:

Met Ala Gly Phe Pro Leu Leu Ala Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Thr Thr Ser Asn Ile
            35                  40                  45

Ala Ser Asn Ser Val His Trp Tyr Gln Leu Val Pro Gly Ala Ala Pro
50                  55                  60

Lys Leu Leu Ile Tyr Ala Asn Asp Gln Arg Ala Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Arg Pro Glu Asp Glu Thr Asp Tyr Tyr Cys Ala Thr Trp Asp
                100                 105                 110

Asp Ser Val Ser Gly Trp Met Phe Gly Gly Gly Thr Lys Leu Thr Val
            115                 120                 125

Leu Gly Gln Pro Lys Ala Ala Pro Ser Val Thr Leu Phe Pro Pro Ser
            130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Asn Lys Tyr Ala Ala Ser Ser Tyr Leu Ser Leu Thr Pro Glu Gln Trp
            195                 200                 205

Lys Ser His Lys Ser Tyr Ser Cys Gln Val Thr His Glu Gly Ser Thr
```

Val Glu Lys Thr Val Ala Pro Thr Glu Cys Ser
225                 230                 235

(2) INFORMATION FOR SEQ ID NO:13:

(i) SEQUENCE CHARACTERISTICS:
        (A) LENGTH: 236 amino acids
        (B) TYPE: amino acid
        (C) STRANDEDNESS: single
        (D) TOPOLOGY: linear (vii) IMMEDIATE SOURCE:
        (A) LIBRARY: SYNONOT01
        (B) CLONE: 3551457

(xi) SEQUENCE DESCRIPTION: SEQ ID NO:13:

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Thr Ser Gly Tyr Ile Ile
            35                  40                  45

Thr Ser Tyr Ala Met His Trp Val Arg Gln Ala Pro Gly Gln Arg Leu
        50                  55                  60

Glu Trp Met Gly Trp Ile Asn Ala Gly Asn Gly Asn Thr Lys Tyr Ser
65                  70                  75                  80

Gln Asn Phe Gln Gly Arg Ile Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Val Trp Ala Gly Glu Phe Thr Ser Phe Asp Tyr
        115                 120                 125

Trp Gly Gln Gly Thr Leu Val Thr Val Ser Ser Ala Ser Pro Thr Ser
130                 135                 140

Pro Lys Val Phe Arg Leu Ser Leu Glu Arg Thr Pro Lys Asp Gly Lys
145                 150                 155                 160

Arg Gly Arg Arg Met Pro Gly Gln Gly Leu Leu Pro Pro Gly Ala Thr
                165                 170                 175

Gln Cys Asp Leu Glu Arg Lys Gly Xaa Arg Thr Leu Thr Gly Lys Lys
            180                 185                 190

Phe Ser Arg Pro Ser Pro Gly Met Pro Ser Gly Gly Pro Val Thr Pro
        195                 200                 205

Arg Asn Gln Ala Arg Leu Asn Thr Cys Gly Pro Lys Glu Ser Gly Pro
            210                 215                 220

Arg Thr Gly Glu Ile Pro Trp Lys Ile Gly Pro Thr
225                 230                 235

(2) INFORMATION FOR SEQ ID NO:14:

(i) SEQUENCE CHARACTERISTICS:
        (A) LENGTH: 1607 base pairs
        (B) TYPE: nucleic acid
        (C) STRANDEDNESS: single
        (D) TOPOLOGY: linear (vii) IMMEDIATE SOURCE:
        (A) LIBRARY: ADENINB01
        (B) CLONE: 021145

(xi) SEQUENCE DESCRIPTION: SEQ ID NO:14:

```
GTTGAAAAAG CCGAGCACAG GTCCCAGCTC AGTGACTCCT GTGCCCCACC ATGGACACAC      60

TTTGCTCCAC GCTCCTGCTG CTGACCATCC CTTCATGGGT CTTGTCCCAG ATCACCTTGA     120

AGGAGTCTGG TCCGACGCTG GTGATACCCA CAGAGACCCT CACGCTGACT TGCACCTTCT     180

CTGGGTTCTC ACTCAGTACT AGTGGAGTGG GTGTGGGCTG GATCCGTCAG CCCCCAGGAA     240

AGGCCCTGGA GTGGCTTGCA CTCATTTATT GGGATGATGA TAAGCGCAAC AGCCCATCTC     300

TGAAGAGCAG GCTCACCATC ACCAAGGACA CCTCCAAAAA CCAGGTGGTC CTTACAATGA     360

CCAACATGGA CCCTGAGGAC ACAGCCACAT ATTACTGTGC ACACAGACAG GGGTATTGTA     420

GTAGTACCAG CTGCTATTAT CAGTGGTTCG ACCCCTGGGG CCAGGGAACC CAGGTCACCG     480

TCTCCTCAGC ATCCCCGACC AGCCCCAAGG TCTTCCCGCT GAGCCTCTGC AGCACCCAGC     540

CAGATGGGAA CGTGGTCATC GCCTGCCTGG TCCAGGGCTT CTTCCCCCAG GAGCCACTCA     600

GTGTGACCTG GAGCGAAAGC GGACAGGGCG TGACCGCCAG AAACTTCCCA CCCAGCCAGG     660

ATGCCTCCGG GGACCTGTAC ACCACGAGCA GCCAGCTGAC CCTGCCGGCC ACACAGTGCC     720

TAGCCGGCAA GTCCGTGACA TGCCACGTGA AGCACTACAC GAATCCCAGC CAGGATGTGA     780

CTGTGCCCTG CCCAGTTCCC TCAACTCCAC CTACCCCATC TCCCTCAACT CCACCTACCC     840

CATCTCCCTC ATGCTGCCAC CCCCGACTGT CACTGCACCG ACCGGCCCTC GAGGACCTGC     900

TCTTAGGTTC AGAAGCGAAC CTCACGTGCA CACTGACCGG CCTGAGAGAT GCCTCAGGTG     960

TCACCTTCAC CTGGACGCCC TCAAGTGGGA AGAGCGCTGT TCAAGGACCA CCTGAGCGTG    1020

ACCTCTGTGG CTGCTACAGC GTGTCCAGTG TCCTGCCTGG CTGTGCCCAG CCATGGAACC    1080

ATGGGGAGAC CTTCACCTGC ACTGCTGCCC ACCCCGAGTT GAAGACCCCA CTAACCGCCA    1140

ACATCACAAA ATCCGGAAAC ACATTCCGGC CCGAGGTCCA CCTGCTGCCG CCGCCGTCGG    1200

AGGAGCTGGC CCTGAACGAG CTGGTGACGC TGACGTGCCT GGCACGTGGC TTCAGCCCCA    1260

AGGATGTGCT GGTTCGCTGG CTGCAGGGGT CACAGGAGCT GCCCCGCGAG AAGTACCTGA    1320

CTTGGGCATC CCGGCAGGAG CCCAGCCAGG GCACCACCAC CTTCGCTGTG ACCAGCATAC    1380

TGCGCGTGGC AGCCGAGGAC TGGAAGAAGG GGGACACCTT CTCCTGCATG GTGGGCCACG    1440

AGGCCCTGCC GCTGGCCTTC ACACAGAAGA CCATCGACCG CTTGGCGGGT AAACCCACCC    1500

ATGTCAATGT GTCTGTTGTC ATGGCGGAGG TGGACGGCAC CTGCTACTGA GCCGCCCGCC    1560

TGTCCCCACC CCTGAATAAA CTCCATGCTC CCCCAAGCAA AAAAAAA                  1607

(2) INFORMATION FOR SEQ ID NO:15:

(i) SEQUENCE CHARACTERISTICS:
        (A) LENGTH: 958 base pairs
        (B) TYPE: nucleic acid
        (C) STRANDEDNESS: single
        (D) TOPOLOGY: linear (vii) IMMEDIATE SOURCE:
        (A) LIBRARY: ADENINB01
        (B) CLONE: 161752

(xi) SEQUENCE DESCRIPTION: SEQ ID NO:15:

TGATTAGGAA CTGACTACCA CCTGCAGGTC AGGGCCAAGG TTATGGGGTC CCAGGTTCAC      60

CTCCTCAGCT TCCTCCTCCT TTGGATCTCT GATACCAGGG CAGAAACGAC ACTCACGCAG     120

TCTCCAGTAT TCATGTCAGC GACTCCAGGA GACAAAGTCA ACATCTCCTG CAAAGCCAGC     180

CAAGACATTG ATGATGATAT GAACTGGTAC CAACAGAAAC CAGGAGAAGT GGTTATTTTC     240

ATTATTCAAG AAGCTACTAC TCTCGTTCCT GGATTCTCAC CTCGATTCAG TGGCAGCGGG     300
```

```
TATGGAACAG ATTTTACCCT CACAATTAAT AACATACAAT CAGAGGATTC TGCATATTAC      360

TTCTGTCTAC AACATGATAA TTTCCCCGTG ACGTTCGGCC AGGGGACCAA GCTGGAGATC      420

AAACGAACTG TGGCTGCACC ATCTGTCTTC ATCTTCCCGC CATCTGATGA GCAGTTGAAA      480

TCTGGAACTG CCTCTGTTGT GTGCCTGCTG AATAACTTCT ATCCCAGAGA GGCCAAAGTA      540

CAGTGGAAGG TGGATAACGC CCTCCAATCG GGTAACTCCC AGGAGAGTGT CACAGAGCAG      600

GACAGCAAGG ACAGCACCTA CAGCCTCAGC AGCACCCTGA CGCTGAGCAA AGCAGACTAC      660

GAGAAACACA AAGTCTACGC CTGCGAAGTC ACCCATCAGG GCCTGAGCTC GCCCGTCACA      720

AAGAGCTTCA ACAGGGGAGA GTGTTAGAGG GAGAAGTGCC CCCACCTGCT CCTCAGTTCC      780

AGCCTGACCC CCTCCCATCC TTTGGCCTCT GACCCTTTTT CCACAGGGGA CCTACCCCTA      840

TTGCGGTCCT CCAGCTCATC TTTCACCTCA CCCCCCTCCT CCTCCTTGGC TTTAATTATG      900

CTAATGTTGG AGGAGAATGA ATAAATAAAG TGAATCTTTG CAAAAAAAAA AAAAAAA         958

(2) INFORMATION FOR SEQ ID NO:16:

(i) SEQUENCE CHARACTERISTICS:
        (A) LENGTH: 3449 base pairs
        (B) TYPE: nucleic acid
        (C) STRANDEDNESS: single
        (D) TOPOLOGY: linear (vii) IMMEDIATE SOURCE:
        (A) LIBRARY: BLADNOT04
        (B) CLONE: 1320068

(xi) SEQUENCE DESCRIPTION: SEQ ID NO:16:

ACACGCAGCT AGCCGGAGCC CGGACCAGGC GCCTGTGCCT CCTCCTCGTC CCTCGCCGCG       60

TCTGCGAACC TGGGAGCCGG CGGGAGCCCG CGCTCGCCAT GTCGGGCGAG CTCAGCAACA      120

GGTTCCAAGG AGGGAAGGCG TTCGGCTTGC TCAAAGCCCG GCAGGAGAGG AGGCTGGCCG      180

AGATCAACCG GGAGTTTCTG TGTGACCAGA AGTACAGTGA TGAAGAGAAC CTTCCAGAAA      240

AGCTCACAGC CTTCAAAGAG AAGTACATGG AGTTTGACCT GAACAATGAA GGCGAGATTG      300

ACCTGATGTC TTTAAAGAGG ATGATGGAGA AGCTTGGTGT CCCCAAGACC CACCTGGAGA      360

TGAAGAAGAT GATCTCAGAG GTGACAGGAG GGGTCAGTGA CACTATATCC TACCGAGACT      420

TTGTGAACAT GATGCTGGGG AAACGGTCGG CTGTCCTCAA GTTAGTCATG ATGTTTGAAG      480

GAAAAGCCAA CGAGAGCAGC CCCAAGCCAG TTGGCCCCCC TCCAGAGAGA GACATTGCTA      540

GCCTGCCCTG AGGACCCCGC CTGGACTCCC CAGCCTTCCC ACCCCATACC TCCCTCCCGA      600

TCTTGCTGCC CTTCTTGACA CACTGTGATC TCTCTCTCTC TCATTTGTTT GGTCATTGAG      660

GGTTTGTTTG TGTTTTCATC AATGTCTTTG TAAAGCACAA ATTATCTGCC TTAAAGGGGC      720

TCTGGGTCGG GGAATCCTGA GCCTTGGGTC CCCTCCCTCT CTTCTTCCCT CCTTCCCCGC      780

TCCCTGTGCA GAAGGGCTGA TATCAAACCA AAAACTAGAG GGGGCAGGGC CAGGGCAGGG      840

AGGCTTCCAG CCTGTGTTCC CCTCACTTGG AGGAACCAGC ACTCTCCATC CTTTCAGAAA      900

GTCTCCAAGC CAAGTTCAGG CTCACTGACC TGGCTCTGAC GAGGACCCCA GGCCACTCTG      960

AGAAGACCTT GGAGTAGGGA CAAGGCTGCA GGGCCTCTTT CGGGTTTCCT TGGACAGTGC     1020

CATGGTTCCA GTGCTCTGGT GTCACCCAGG ACACAGCCAC TCGGGCCCC GCTGCCCCAG     1080

CTGATCCCCA CTCATTCCAC ACCTCTTCTC ATCCTCAGTG ATGTGAAGGT GGGAAGGAAA     1140

GGAGCTTGGC ATTGGGAGCC CTTCAAGAAG GTACCAGAAG GAACCCTCCA GTCCTGCTCT     1200

CTGGCCACAC CTGTGCAGGC AGCTGAGAGG CAGCGTGCAG CCCTACTGTC CCTTACTGGG     1260
```

```
GCAGCAGAGG GCTTCGGAGG CAGAAGTGAG GCCTGGGGTT TGGGGGGAAA GGTCAGCTCA      1320

GTGCTGTTCC ACCTTTTAGG GAGGATACTG AGGGGACCAG GATGGGAGAA TGAGGAGTAA      1380

AATGCTCACG GCAAAGTCAG CAGCACTGGT AAGCCAAGAC TGAGAAATAC AAGGTTGCTT      1440

GTCTGACCCC AATCTGCTTG AAACCTGACT CTGCTTCTCT CATTTGTCTT CCTACCCTAC      1500

TCACATAATT CACTCATTGA CTCACTCATT CACCAGATAT TTATTGACCT GCTATTATAA      1560

GCTTTACATC CTCCCATGTT GTCCTGGCAT GTGCAGTATA CACGGTCTAA CTCATCTCTC      1620

CCCAGATCTC TCAGAACCTT GAGCTTGGGA ATTGAACTGG GGTCACCTGT GTCCTTTCTT      1680

ATGGACTCGC AGGATTTTAG AACCCTAATG CACCCTGGAG GGTAGCTGGG CCAGACTTCT      1740

CATTTCACAG GTGAGGAGAC TGGTGCCCCA CAGGGATTAA GTGCCTTGCC CAAGGTCAGG      1800

CTTATCTCCA GAGGGAGGTG CCCTGGACTG GGGCCCAGAT GTTCAGGGAC CCTGCCTACA      1860

CCTCATTTCC AGTGTGGGCT GCCTTAGTTA GTTATGAGAA CAGGGAAGGG CTGGGAAGAG      1920

ACAGCCTCCA AGGTCAACAC TTGGAGAGGG TTTCACTTGC TCTGAAGACC CTGGTCCAGG      1980

ATTCGCCCTC TCCCATGCCT TCAAGTCAGC ATCAGGCTTA GGGCAAAGAC CAGGCCTCTG      2040

AAGCTGCCTC TTGTAATTCA TGCAGGAAGA TGTCAAAGTC AGCCCCATCT TGGCTGATCA      2100

GGGTGTTCAG CCTTAACCCC ACCTGTGTTC TGAAGTCTCT TACCCTACCT GCTCAGGACT      2160

GAGACAGTTA TTCACTGAAC ATATTTATTA AGCACTTGCT GTAGGCCAAC AGTTAAGAAT      2220

CCAATAATGA AATGGACAGA TTCATGGAAC TTAGAGTCCA ATAGGAAAGT GAGACCCAGA      2280

CAATGACAAT GAGATAAATG TTAGGAAGGG GGAGGTATGG GGTGACTTCC CTGCAGTCCT      2340

GGGGGCCTAG ATGGGCCCAA GACTGGGTGA GAGTCTTGGC AGAGGCTTTG CAACACCTTA      2400

AGTGGACAGG ACTGGGAGGT CTTGGTGGTT GGAGCCAACG TGGGTTCCCT GCGGCTCCTT      2460

AGTCACCTCT GATAGCAGAT TGAGGGAGGA AAACAGGTAA GGCATGAGGA AATGGCCAGG      2520

TTGGGTTAAC CCACTGGTTT CAACCAGTTC AGGAATGAGG TTATTTGGCC ATGACTGGCT      2580

GATCTTGAGC TCAAGGATCT GCTTCAAATG CACACAGGCC TAGTTGAAGT TTAAACCCCA      2640

GCAAAACATT CCTCCCTGTA AATGGAAAAT CCTACTTCTA CCCCCACCCT GCCCTGTTTT      2700

TTGTTTTTTT TTTTCCCCAA GATCATTAGA TGTCCTCACC CCTCCTCACT GCCTCTCCTC      2760

TCTGGGACAG GCTGGGACCT TTGAGGAAGA TAAAGCCTTC CTTGACTACC CATCATATTC      2820

AGTGTCCCTG TTCCTCACTC AGAGAGGAAG GCAGAACCAG TCAGGCTTAT TTCAGTAAGT      2880

TCCACAGTTC TACAAGACTG CAGGAATTCT CCTTAAGGGA GGAGAGCAAG CAGGTGTGGC      2940

CCCAGCTTCT GGAAATGGCA GAAGAGAGGG TTTTCTCATT GAATGGGGGT GGGGGCTCGT      3000

GTGTCCTGGG AAACCCCATC AGTCCCTTCA TTTCTTGAGA CTCAACTCCT GGGAGGAGAG      3060

GGTCTCAAGA GTTGTCCCTG GAAGGAGGGC GGGGGCAGTC TGCATCTATT TCAGGTTGTG      3120

GCTCTTGGTT CTAGGACTCT TACTTCTCTG GCTAAGGGCT CAGCTTCTTG GGACTTCAAC      3180

CATCTTCTTT CTGAAAGACC AAATCTAATG TAACCAGTAA CGTGAGGACT GCCAAGTATG      3240

GCTTTGTCCC TATGACTCAG AGGAGGGTTT GTCGGGCAAA TTCAGGTGGA TGAAGTATGT      3300

GTGTGCGTGT GCATGGGAGT GTGCGTGGAC TGGGATATCA TCTCTACAGC CTGCAAATAA      3360

ACCAGACAAA CTTACCAACG TCTTGATTGG TGTATTTTGG GGCTGGTTCT GGGCTCAGCA      3420

AATTGCGGAC TAGCTAATAT AGTAAGAGG                                       3449
```

(2) INFORMATION FOR SEQ ID NO:17:

(i) SEQUENCE CHARACTERISTICS:

(A) LENGTH: 1567 base pairs
        (B) TYPE: nucleic acid
        (C) STRANDEDNESS: single
        (D) TOPOLOGY: linear (vii) IMMEDIATE SOURCE:
        (A) LIBRARY: PANCTUT01
        (B) CLONE: 1513264

(xi) SEQUENCE DESCRIPTION: SEQ ID NO:17:

```
CACACATTTC CTTGAATTCA GGGTCCAGCT CACATGGGAA ATACTTTCTG AGAGTCCTGG      60
ACCTCCTGTG CAAGAACATG AAACACCTGT GGTTCTTCCT CCTGCTGGTG GCAGCTCCCA     120
GATGGGTCCT GTCCCAGGTG CAGCTGCAGG AGTCGGGCCC AGGACTGGTG AAGCCTTCGG     180
AGACCCTGTC CCTCACCTGC GCTGTCTCTG GTGGCTCCAT CACTAGTGGT GGTTACTACT     240
GGAGCTGGAT CCGCCAGCCC CCAGGGAAGG GGCTGGAGTG GATTGGGTAC ATCTATTACA     300
GTGGGAGCAC CCTCTACAAC CCGTCCCTCA AGAGTCGAGT TACCATATCA GTAGACACGT     360
CCAAGAACCA GTTCTCCCTG AAGCTGAGCT CTGTGACTGC CGCAGACACG GCCGTGTATT     420
ACTGTGCCAG AGATGACGTA GGTTTAAGGG GGGGAACTA CGGTATGGAC GTCTGGGGCC      480
AGGGAACCCT GGTCACCGTC TCCTCAGCCT CCACCAAGGG CCCATCGGTC TTCCCCCTGG     540
CACCCTCCTC CAAGAGCACC TCTGGGGGCA CAGCGGCCCT GGGCTGCCTG GTCAAGGACT     600
ACTTCCCCGA ACCGGTGACG GTGTCGTGGA ACTCAGGCGC CCTGACCAGC GGCGTGCACA     660
CCTTCCCGGC TGTCCTACAG TCCTCAGGAC TCTACTCCCT CAGCAGCGTG GTGACCGTGC     720
CCTCCAGCAG CTTGGGCACC CAGACCTACA TCTGCAACGT GAATCACAAG CCCAGCAACA     780
CCAAGGTGGA CAAGAGAGTT GAGCCCAAAT CTTGTGACAA AACTCACACA TGCCCACCGT     840
GCCCAGCACC TGAACTCCTG GGGGGACCGT CAGTCTTCCT CTTCCCCCCA AAACCCAAGG     900
ACACCCTCAT GATCTCCCGG ACCCCTGAGG TCACATGCGT GGTGGTGGAC GTGAGCCACG     960
AAGACCCTGA GGTCAAGTTC AACTGGTACG TGGACGGCGT GGAGGTGCAT AATGCCAAGA    1020
CAAAGCCGCG GGAGGAGCAG TACAACAGCA CGTACCGTGT GGTCAGCGTC CTCACCGTCC    1080
TGCACCAGGA CTGGCTGAAT GGCAAGGAGT ACAAGTGCAA GGTCTCCAAC AAAGCCCTCC    1140
CAGCCCCCAT CGAGAAAACC ATCTCCAAAG CCAAAGGGCA GCCCCGAGAA CCACAGGTGT    1200
ACACCCTGCC CCCATCCCGG GAGGAGATGA CCAAGAACCA GGTCAGCCTG ACCTGCCTGG    1260
TCAAAGGCTT CTATCCCAGC GACATCGCCG TGGAGTGGGA GAGCAATGGG CAGCCGGAGA    1320
ACAACTACAA GACCACGCCT CCCGTGCTGG ACTCCGACGG CTCCTTCTTC CTCTACAGCA    1380
AGCTCACCGT GGACAAGAGC AGGTGGCAGC AGGGGAACGT TTTCTCATGC TCCGTGATGC    1440
ATGAGGCTCT GCACAACCAC TACACACAGA AGAGCCTCTC CCTGTCCCCG GGTAAATGAG    1500
TGCCAGGGCC GGCAAGCCCC CGTTCCCCGG GCTCTCGGGG TCGCGCGAGG TTTCTTTTNA    1560
AGTTACG                                                             1567
```

(2) INFORMATION FOR SEQ ID NO:18:

(i) SEQUENCE CHARACTERISTICS:
        (A) LENGTH: 1572 base pairs
        (B) TYPE: nucleic acid
        (C) STRANDEDNESS: single
        (D) TOPOLOGY: linear (vii) IMMEDIATE SOURCE:
        (A) LIBRARY: BMARNOT03
        (B) CLONE: 1669829

(xi) SEQUENCE DESCRIPTION: SEQ ID NO:18:

```
CCCAGCCCTG AGATTCCCAG GTGTTTCCAC TCAGTGATCA GCACTGAACA CAGAGGACTC      60

ACCATGGAGT TGGGACTGAG CTGGATTTTC CTTTTGGCTA TTTTAAAAGG TGTCCAGTGT     120

GAAGTGCAGC TGGTGGAGTC TGGGGGAGGC TTGGTACAGC CTGGCAGGTC CCTGAGACTC     180

TCCTGTGCAG CCTCTGGATT CACTTTTGAT GACCATGCCA TGCACTGGGT CCGGCAAATT     240

CCAGGGAAGG GCCTGGAGTG GGTCTCAGGT ATTAATTGGC ATAGTGTTAC CATAGGCTAT     300

GCGAACTCTG TAAAGGGCCG ATTCACCATC TCCAGAGACA ACGCCAAGAG CTCCCTGTAT     360

CTGCAAATGA ACAGTCTGAG AGTTGAGGAC ACGGCTTTGA ATAATTGGGC TAAAGATTTG     420

AAGACCCCAA GGGGTGGATA CAGTGCTTCA ATGGACTACT GGGGCCAGGG AACCCTGGTC     480

ATCGTCTCCT CAGCATCCCC GACCAGCCCC AAGGTCTTCC CGCTGAGCCT CGACAGCACC     540

CCCCAAGATG GAACGTGGT CGTCGCATGC CTGGTCCAGG GCTTCTTCCC CCAGGAGCCA      600

CTCAGTGTGA CCTGGAGCGA AAGCGGACAG AACGTGACCG CCAGAAACTT CCCACCTAGC     660

CAGGATGCCT CCGGGGACCT GTACACCACG AGCAGCCAGC TGACCCTGCC GGCCACACAG     720

TGCCCAGACG GCAAGTCCGT GACATGCCAC GTGAAGCACT ACACGAATCC CAGCCAGGAT     780

GTGACTGTGC CCTGCCCAGT TCCCCCACCT CCCCCATGCT GCCACCCCCG ACTGTCGCTG     840

CACCGACCGG CCCTCGAGGA CCTGCTCTTA GGTTCAGAAG CGAACCTCAC GTGCACACTG     900

ACCGGCCTGA GAGATGCCTC TGGTGCCACC TTCACCTGGA CGCCCTCAAG TGGGAAGAGC     960

GCTGTTCAAG GACCACCTGA GCGTGACCTC TGTGGCTGCT ACAGCGTGTC CAGTGTCCTG    1020

CCTGGCTGTG CCCAGCCATG GAACCATGGG GAGACCTTCA CCTGCACTGC TGCCCACCCC    1080

GAGTTGAAGA CCCCACTAAC CGCCAACATC ACAAAATCCG GAAACACATT CCGGCCCGAG    1140

GTCCACCTGC TGCCGCCGCC GTCGGAGGAG CTGGCCCTGA ACGAGCTGGT GACGCTGACG    1200

TGCCTGGCAC GTGGCTTCAG CCCCAAGGAT GTGCTGGTTC GCTGGCTGCA GGGGTCACAG    1260

GAGCTGCCCC GCGAGAAGTA CCTGACTTGG GCATCCCGGC AGGAGCCCAG CCAGGGCACC    1320

ACCACCTTCG CTGTGACCAG CATACTGCGC GTGGCAGCCG AGGACTGGAA GAAGGGGGAC    1380

ACCTTCTCCT GCATGGTGGG CCACGAGGCC CTGCCGCTGG CCTTCACACA GAAGACCATC    1440

GACCGCTTGG CGGGTAAACC CACCCATGTC AATGTGTCTG TTGTCATGGC GGAGGTGGAC    1500

GGCACCTGCT ACTGAGCCGC CGCCTGTCC CCACCCCTGA ATAAACTCCA TGCTCCCCCA    1560

AGCAAAAAAA AA                                                        1572

(2) INFORMATION FOR SEQ ID NO:19:

(i) SEQUENCE CHARACTERISTICS:
          (A) LENGTH: 931 base pairs
          (B) TYPE: nucleic acid
          (C) STRANDEDNESS: single
          (D) TOPOLOGY: linear (vii) IMMEDIATE SOURCE:
          (A) LIBRARY: COLSUCT01
          (B) CLONE: 2280869

(xi) SEQUENCE DESCRIPTION: SEQ ID NO:19:

GACCCAGACG GAACCATGGA AGCCCCAGCG CAGCTTCTCT TCCTCCTGCT GCTCTGGCTC      60

CCAGATTCCT TTGGAGAAAT TGTAATGACG CAGTCTCCAG CCATCGTGTC TCTGTCTCCA     120

GGGGAAAGAG CCACCCTTTC CTGCAGGGCC AGTCAGTCTA TTGGCAGCAC CATCGCCTGG     180

TACCAACAAA GACCTGGCCA GTCTCCCAGG CTCCTCATCT ATGGTGCTTC CACCCGGGCC     240

ACTGGTGTCC CACCCAGGTT CAGTGGCGGT GGGTCTGGGA CAGAGTTCAC TCTCTTCATC     300
```

```
AGCAGCCTGC AGTCTGAAGA TTTTGCACTT TATTACTGTC AGCAGTATAA AGGCTGGCCG      360

CTCACTTTCG GCGGAGGGAC CAGGGTGCAG ATCAAACGAA CTGTGGCTGC ACCATCTGTC      420

TTCATCTTCC CGCCATCTGA TGAGCAGTTG AAATCTGGAA CTGCCTCTGT TGTGTGCCTG      480

CTGAATAACT TCTATCCCAG AGAGGCCAAA GTACAGTGGA AGGTGGATAA CGCCCTCCAA      540

TCGGGTAACT CCCAGGAGAG TGTCACAGAG CAGGACAGCA AGGACAGCAC CTACAGCCTC      600

AGCAGCACCC TGACGCTGAG CAAAGCAGAC TACGAGAAAC ACAAAGTCTA CGCCTGCGAA      660

GTCACCCATC AGGGCCTGAG CTCGCCCGTC ACAAAGAGCT TCAACAGGGG AGAGTGTTAG      720

AGGGAGAAGT GCCCCCACCT GCTCCTCAGT TCCAGCCTGA CCCCCTCCCA TCCTTTGGCC      780

TCTGACCCTT TTTCCACAGG GGACCTACCC CTATTGCGGT CCTCCAGCTC ATCTTTCACC      840

TCACCCCCCT CCTCCTCCTT GGCTTTAATT ATGCTAATGT TGGAGGAGAA TGAATAAATA      900

AAGTGAATCT TTGCAAAAAA AAAAAAAAAA A                                    931

(2) INFORMATION FOR SEQ ID NO:20:

(i) SEQUENCE CHARACTERISTICS:
        (A) LENGTH: 935 base pairs
        (B) TYPE: nucleic acid
        (C) STRANDEDNESS: single
        (D) TOPOLOGY: linear (vii) IMMEDIATE SOURCE:
        (A) LIBRARY: ADRETUT05
        (B) CLONE: 2492122

(xi) SEQUENCE DESCRIPTION: SEQ ID NO:20:

GGGCAGGGAG AGATTTGGGG AGGCTCTGCT TCAGCTGTGG GCACAAGAGG CAGCACTCAG       60

GACAATCTCC AGCATGGCCT GGTCTCCTCT CCTCCTCACT CTCCTCGCTC ACTGCACAGG      120

GTCCTGGGCC CAGTCTGTGC TGACGCAGCC GCCCTCAGTG TCTGGGGCCC CAGGGCAGAG      180

GGTCACCATC TCCTGCACTG GGAGCAGCTC CAACATCGGG GCAGGTTATG ATGTACACTG      240

GTACCAGCAG CTTCCAGGAA CAGCCCCCAA ACTCCTCATC TATGGTAGTA GAAATCGGCC      300

CTCAGGGGTC CCTGACCGAT TCTCTGGCTC CAAGTCTGGC ACCTCAGCCT CCCTGGCCAT      360

CACTGGGCTC CAGGCTGAGG ATGAGGCTGA TTATTACTGC CAGTCCTATG ACAGCAGCCT      420

GAGTGGTGTG GTATTCGGCG GAGGGACCAA GCTGACCGTC CTCGGTCAGC CCAAGGCTGC      480

CCCCTCGGTC ACTCTGTTCC CGCCCTCCTC TGAGGAGCTT CAAGCCAACA GGGCCACACT      540

GGTGTGTCTC ATAAGTGACT TCTACCCGGG AGCCGTGACA GTGGCCTGGA AGGCAGATAG      600

CAGCCCCGTC AAGGCGGGAG TGGAGACCAC CACACCCTCC AAACAAAGCA ACAACAAGTA      660

CGCGGCCAGC AGCTACCTGA GCCTGACGCC TGAGCAGTGG AAGTCCCACA GAAGCTACAG      720

CTGCCAGGTC ACGCATGAAG GGAGCACCGT GGAGAAGACA GTGGCCCCTA CAGAATGTTC      780

ATAGGTTCTA AACCCTCACC CCCCACCACG GGAGACTAGA GCTGCAGGAT CCCAGGGGAG      840

GGGTCTCTCC TCCCACCCCA AGGCATCAAG CCCTTCTCCC TGCACTCAAT AAACCCTCAA      900

TAAATATTCT CATTGTCAAT CAGAAAAAAA AAAAA                                935

(2) INFORMATION FOR SEQ ID NO:21:

(i) SEQUENCE CHARACTERISTICS:
        (A) LENGTH: 1655 base pairs
        (B) TYPE: nucleic acid
        (C) STRANDEDNESS: single
        (D) TOPOLOGY: linear
```

(vii) IMMEDIATE SOURCE:
    (A) LIBRARY: LUNGTUT11
    (B) CLONE: 2747531

(xi) SEQUENCE DESCRIPTION: SEQ ID NO:21:

| | | | | | |
|---|---|---|---|---|---|
| GCCACATCCC | TCCCCTACAG | AAGCCCCCAG | AGTGCAGCTC | CTCACCATGG | ACTGCACCTG | 60 |
| GAGGATCCTC | TTCTTGGTGG | CAGCAGCTAC | AGGCACCCAC | GCCCAGGTCC | AGTTGGTACA | 120 |
| GTCTGGGGCT | GAGGTGAAGA | AGCCTGGGGC | CTCAGTGCAG | GTCTCCTGCA | CGGTTTCCGG | 180 |
| ATTCACCCTC | AGTGATTTAT | CCGTGCACTG | GGTGCGACAG | GCTCCTGGAC | AAGGGCTTGA | 240 |
| GTGGATGGGA | GGTTTAGCTC | CTGAAAATGG | AGAGGCAGTC | TACGCACAGA | AATTCCTGGG | 300 |
| CAGACTCACC | TTGTCCGAGG | ACACATCTGC | AGACACAGCC | TACATGTTTC | TGAACAACCT | 360 |
| AGGATCTGAG | GACTCGGCCA | TCTATTACTG | TGCAAGACAA | CATTACGATT | TTTTCTTCGA | 420 |
| CTTCTGGGGC | CAGGGGACAA | TGGTCACCGT | CTCTTCAGCC | TCCACCAAGG | GCCCATCGGT | 480 |
| CTTCCCCCTG | GCACCCTCCT | CCAAGAGCAC | CTCTGGGGGC | ACAGCGGCCC | TGGGCTGCCT | 540 |
| GGTCAAGGAC | TACTTCCCCG | AACCGGTGAC | GGTGTCGTGG | AACTCAGGCG | CCCTGACCAG | 600 |
| CGGCGTGCAC | ACCTTCCCGG | CTGTCCTACA | GTCCTCAGGA | CTCTACTCCC | TCAGCAGCGT | 660 |
| GGTGACCGTG | CCCTCCAGCA | GCTTGGGCAC | CCAGACCTAC | ATCTGCAACG | TGAATCACAA | 720 |
| GCCCAGCAAC | ACCAAGGTGG | ACAAGAAAGT | TGAGCCCAAA | TCTTGTGACA | AAACTCACAC | 780 |
| ATGCCCACCG | TGCCCAGCAC | CTGAACTCCT | GGGGGGACCG | TCAGTCTTCC | TCTTCCCCCC | 840 |
| AAAACCCAAG | GACACCCTCA | TGATCTCCCG | GACCCCTGAG | GTCACATGCG | TGGTGGTGGA | 900 |
| CGTGAGCCAC | GAAGACCCTG | AGGTCAAGTT | CAACTGGTAC | GTGGACGGCG | TGGAGGTGCA | 960 |
| TAATGCCAAG | ACAAAGCCGC | GGGAGGAGCA | GTACAACAGC | ACGTACCGTG | TGGTCAGCGT | 1020 |
| CCTCACCGTC | CTGCACCAGG | ACTGGCTGAA | TGGCAAGGAG | TACAAGTGCA | AGGTCTCCAA | 1080 |
| CAAAGCCCTC | CCAGCCCCCA | TCGAGAAAAC | CATCTCCAAA | GCCAAAGGGC | AGCCCCGAGA | 1140 |
| ACCACAGGTG | TACACCCTGC | CCCCATCCCG | GGAGGAGATG | ACCAAGAACC | AGGTCAGCCT | 1200 |
| GACCTGCCTG | GTCAAAGGCT | TCTATCCCAG | CGACATCGCC | GTGGAGTGGG | AGAGCAATGG | 1260 |
| GCAGCCGGAG | AACAACTACA | AGACCACGCC | TCCCGTGCTG | GACTCCGACG | GCTCCTTCTT | 1320 |
| CCTCTATAGC | AAGCTCACCG | TGGACAAGAG | CAGGTGGCAG | CAGGGGAACG | TCTTCTCATG | 1380 |
| CTCCGTGATG | CATGAGGCTC | TGCACAACCA | CTACACGCAG | AAGAGCCTCT | CCCTGTCCCC | 1440 |
| GGGTAAATGA | GTGCGACGGC | CGGCAAGCCC | CCGCTCCCCG | GCTCTCGCG | GTCGCACGAG | 1500 |
| GATGCTTGGC | ACGTACCCCC | TGTACATACT | TCCCAGGCAC | CCAGCATGGA | AATAAAGCAC | 1560 |
| CCACCATTTG | CCTGGGCCCT | TCGAAAAACA | AAAAAAANCC | NNNACCAANC | ACACCCCNCA | 1620 |
| AANCCACAAA | AAAAAAAAAC | TTGGGGGGGG | CCCTC | | | 1655 |

(2) INFORMATION FOR SEQ ID NO:22:

(i) SEQUENCE CHARACTERISTICS:
      (A) LENGTH: 1818 base pairs
      (B) TYPE: nucleic acid
      (C) STRANDEDNESS: single
      (D) TOPOLOGY: linear (vii) IMMEDIATE SOURCE:
      (A) LIBRARY: BRSTNOT13
      (B) CLONE: 2784232

(xi) SEQUENCE DESCRIPTION: SEQ ID NO:22:

TCCCAATCAG TTTCCAGCCA ACACCAGGGT GTCCTAGTCC GCAGAGGTGT GGGGGACACA    60

-continued

```
CTCCATAATC TCTACTTTTC TTTTTGTGCA GCTGAGTCAT GGAGCTTTCA GCCCCAGCAC    120

ATGGCTCCTC CTTAACTGCG TCTGCTCAAC CTCCCTCAGC CCTGTGAACA GCATCCCCGC    180

ACACAGACGC AGAGCAGGAC TCTCTCTGCT GCCACTTCAC CTTCCTGAGA GAGGACCAGC    240

GGCCAGAGCC TCAGTGACTG CCACCCTGGA GGACAGGGCA CAACAACCGT TTCTGGAGAG    300

AATGGGAGGA TTCCAGAGGG GCAAATATGG AACTATGGCT GAAGGTAGAT CAGAAGATAA    360

CTTGTCTGCA ACACCACCGG CATTGAGGAT TATCCTAGTG GGCAAAACAG GCTGCGGGAA    420

AAGTGCCACA GGGAACAGCA TCCTTGGCCA GCCCGTGTTT GAGTCCAAGC TGAGGGCCCA    480

GTCAGTGACC AGGACGTGCC AGGTGAAAAC AGGAACATGG AACGGGAGGA AAGTCCTGGT    540

GGTTGACACG CCCTCCATCT TTGAGTCACA GGCCGATACC CAAGAGCTGT ACAAGAACAT    600

CGGGGACTGC TACCTGCTCT CTGCCCCGGG GCCCCACGTC CTGCTTCTGG TGATCCAGCT    660

GGGGCGTTTC ACTGCTCAGG ACACAGTGGC CATCAGGAAG GTGAAAGAGG TCTTTGGGAC    720

AGGGGCCATG AGACATGTGG TCATCCTCTT CACCCACAAA GAGGACTTAG GGGGCCAGGC    780

CCTGGATGAC TATGTAGCAA ACACGGACAA CTGCAGCCTG AAAGACCTGG TGCGGGAGTG    840

TGAGAGAAGG TACTGTGCCT TCAACAACTG GGCTCTGTG GAGGAGCAGA GGCAGCAGCA    900

GGCAGAGCTC CTGGCTGTGA TTGAGAGGCT GGGGAGGGAG CGAGAGGGCT CCTTCCACAG    960

CAATGACCTC TTCTTGGATG CCCAGCTGCT CCAAAGAACT GGAGCTGGGG CCTGCCAGGA    1020

AGACTACAGG CAGTACCAGG CCAAAGTGGA ATGGCAGGTG GAGAAGCACA AGCAAGAGCT    1080

GAGGGAGAAC GAGAGTAACT GGGCATACAA GGCGCTCCTC AGAGTCAAAC ACTTGATGCT    1140

TTTGCATTAT GAGATTTTTG TTTTTCTATT GTTGTGCAGC ATACTTTTTT TCATTATTTT    1200

TCTGTTCATC TTTCATTACA TTTAAATCTC TGGACCCTGG AGCACTTCTA ATGTATCACC    1260

CCATGGAGTC ATTGTTCTAA TAATCACCAA TTCAGACTCA GATCCTCGTG GTCTATGGAG    1320

CATGCTGCTT GCTGTCTGTG CAGCTCCCAT TTCCCCTTCT TCCTGATAGA CTTGGAGCTG    1380

TGTGCCTCCA CTCCAAGGCT GCCTGCCTGC TGTAAACACT ATTCCACTCT GTCTGCCAAC    1440

AACTGCTTCA GGAATGGGCC TGAGATCCCA TGCAGGTCCC TGAGAAGTGA GTAAAAGTCC    1500

GCAGAGGTGG GGATGGAAGA TCTCTCCTTA GATAGAACCT GTCTTCCTCC CTGGCATTGT    1560

GGGGTCTGGG CGTGACACTG GGACTCTCAG CAGCTTTGTG CTGCCAACCT GAGATTGAAG    1620

GCAGTGCCTC AGAGCAGCAC AGAGAGTTGG GGCCCCCTGA GCCCTGAGCC ACCAGCCCTG    1680

CAGCCTGCCC TATCTCCGCA TTTCCAGTTG TATTAGCCAA TAGATTTCCT ACTTATTTAA    1740

GCTATTTGAG CTCCGGGTCT CTTCTACCTG CATTCTAAAA CATTCAAAGT AATAAAAATT    1800

TCTCCACAAA AAAAAAAA                                                  1818
```

(2) INFORMATION FOR SEQ ID NO:23:

(i) SEQUENCE CHARACTERISTICS:
        (A) LENGTH: 891 base pairs
        (B) TYPE: nucleic acid
        (C) STRANDEDNESS: single
        (D) TOPOLOGY: linear (vii) IMMEDIATE SOURCE:
        (A) LIBRARY: THYRNOT10
        (B) CLONE: 2872705

(xi) SEQUENCE DESCRIPTION: SEQ ID NO:23:

```
CGGCTCGAGC AGCGCTCTCG GGACGTCTCC ACCATGGCCT GGGCTCTGCT ATTCCTCACC     60

CTCCTCACTC AGGGCACAGG GTCCTGGGCC CAGTCTGCCC TGACTCAGCC TGCCTCCGTG    120
```

-continued

```
TCTGGGTCTC CTGGACAGTC GATCACCATC TCCTGCACTG GAACCAGCAG TGACGTTGGT        180

GGTTATAACT ATGTCTCCTG GTACCAACAG TCCCCAGGCA CGGCCCCCAA ACTCATGATT        240

TATGAGGTCA GTAATCGGCC CTCAGGGGTT TCTAATCGGT TCTCTGGCTC CAAGTCTGGC        300

AACACGGCCT CCCTGACCAT CTCTGGGCTC CAGGCTGAGG ACGAGGCTGA TTATTACTGC        360

AGCTCATATG TAGGCAACAA CATTGTGGTA TTCGGCGGAG GGACCAAGCT GACCGTCCTA        420

GGTCAGCCCA AGGCTGCCCC CTCGGTCACT CTGTTCCCGC CTCCTCTGA GGAGCTTCAA         480

GCCAACAAGG CCACACTGGT GTGTCTCATA AGTGACTTCT ACCCGGGAGC CGTGACAGTG        540

GCCTGGAAGG CAGATAGCAG CCCCGTCAAG GCGGGAGTGG AGACCACCAC ACCCTCCAAA        600

CAAAGCAACA ACAAGTACGC GGCCAGCAGC TATCTGAGCC TGACGCCTGA GCAGTGGAAG        660

TCCCACAGAA GCTACAGCTG CCAGGTCACG CATGAAGGGA GCACCGTGGA GAAGACAGTG        720

GCCCCTACAG AATGTTCATA GGTTCTAAAC CCTCACCCCC CCACGGGAG ACTAGAGCTG         780

CAGGATCCCA GGGGAGGGGT CTCTCCTCCC ACCCCAAGGC ATCAAGCCCT TCTCCCTGCA        840

CTCAATAAAC CCTCAATAAA TATTCTCATT GTCAATCAGA AAAAAAAAA A                  891
```

(2) INFORMATION FOR SEQ ID NO:24:

(i) SEQUENCE CHARACTERISTICS:
        (A) LENGTH: 919 base pairs
        (B) TYPE: nucleic acid
        (C) STRANDEDNESS: single
        (D) TOPOLOGY: linear (vii) IMMEDIATE SOURCE:
        (A) LIBRARY: LNODNOT08
        (B) CLONE: 3056213

(xi) SEQUENCE DESCRIPTION: SEQ ID NO:24:

```
GAGGAAAACA ACGCCCCAGC TGGGAAGCCT GAGAACACTT AGCCTTCATG AGTGTCCCCA         60

CCATGGCCTG GATGATGCTT CTCCTCGGAC TCCTTGCTTA TGGATCAGGA GTGGATTCTC        120

AGACTGTGGT GACCCAGGAG CCATCGTTCT CAGTGTCCCC TGGAGGGACA GTCACACTCA        180

CTTGTGGCTT GAGCTCTGGC TCAGTCTCTA CTAGTAACTA CCCCAGCTGG TACCAGCAGA        240

CCCCAGGCCA GGCTCCACGC ACGCTCATAT ACGGCACAAG TGTTCGTTCT TCTGGAGTCC        300

CTGATCGCTT CTCTGGCTCC ATCCTTGGGA ACAAAGCCGG CCTCACCATC ACGGGGGCCC        360

AGGCAGATGA TGAATCTGAT TATTATTGTG TCCTATATAG GCGTAGTGGC TCTTGGGTGT        420

TCGGCGGAGG GACCAAGCTG TCCGTCCTAG GTCAGCCCAA GGCTGCCCCC TCGGTCACTC        480

TGTTCCCACC CTCCTCTGAG GAGCTTCAAG CCAACAAGGC CACACTGGTG TGTCTCATAA        540

GTGACTTCTA CCCGGGAGCC GTGACAGTGG CCTGGAAGGC AGATAGCAGC CCCGTCAAGG        600

CGGGAGTGGA GACCACCACA CCCTCCAAAC AAAGCAACAA CAAGTACGCG GCCAGCAGCT        660

ACCTGAGCCT GACGCCTGAG CAGTGGAAGT CCCACAAAAG CTACAGCTGC CAGGTCACGC        720

ATGAAGGGAG CACCGTGGAG AAGACAGTGG CCCCTACAGA ATGTTCATAG GTTCTCATCC        780

CTCACCCCCC ACCACGGGAG ACTAGAGCTG CAGGATCCCA GGGGAGGGGT CTCTCCTCCC        840

ACCCCAAGGC ATCAAGCCCT TCTCCCTGCA CTCAATAAAC CCTCAATAAA TATTCTCATT        900

GTCAATCAAA AAAAAAAA                                                      919
```

(2) INFORMATION FOR SEQ ID NO:25:

(i) SEQUENCE CHARACTERISTICS:
        (A) LENGTH: 895 base pairs
        (B) TYPE: nucleic acid

```
        (C) STRANDEDNESS: single
        (D) TOPOLOGY: linear (vii) IMMEDIATE SOURCE:
        (A) LIBRARY: LUNGTUT13
        (B) CLONE: 3116314

(xi) SEQUENCE DESCRIPTION: SEQ ID NO:25:

TGGCGAGAGA AGACAGGATT CAGGACAATC TCCAGCATGG CCGGCTTCCC TCTCCTCCTC      60

GCCCTCCTCA CTCACTGTGC AGGGTCCTGG GCCCAGTCTG TGCTGACTCA GCCCCCCTCA     120

GCGTCTGGGA CCCCCGGGCA GAGGGTCACC ATCTCTTGTT CTGGAACCAC CTCCAACATC     180

GCAAGTAATT CTGTGCATTG GTACCAATTA GTTCCAGGAG CGGCCCCCAA ACTCCTCATC     240

TATGCTAATG ATCAGCGTGC CTCCGGGGTC CCTGACCGAT TCTCTGGCTC CAAGTCTGGC     300

ACCTCAGCCT CCCTGGCCAT CAGTGGGCTC CGGCCCGAGG ATGAAACTGA TTATTACTGT     360

GCAACATGGG ATGACAGTGT CAGTGGTTGG ATGTTCGGCG GAGGGACCAA GCTGACCGTC     420

CTAGGTCAGC CCAAGGCTGC CCCCTCGGTC ACTCTGTTCC CACCCTCCTC TGAGGAGCTT     480

CAAGCCAACA AGGCCACACT GGTGTGTCTC ATAAGTGACT TCTACCCGGG AGCCGTGACA     540

GTGGCCTGGA AGGCAGATAG CAGCCCCGTC AAGGCGGGAG TGGAGACCAC CACACCCTCC     600

AAACAAAGCA ACAACAAGTA CGCGGCCAGC AGCTACCTGA GCCTGACGCC TGAGCAGTGG     660

AAGTCCCACA AAGCTACAG CTGCCAGGTC ACGCATGAAG GGAGCACCGT GGAGAAGACA     720

GTGGCCCCTA CAGAATGTTC ATAGGTTCTC ATCCCTCACC CCCCACCACG GGAGACTAGA     780

GCTGCAGGAT CCCAGGGGAG GGGTCTCTCC TCCCACCCCA AGGCATCAAG CCCTTCTCCC     840

TGCACTCAAT AAACCCTCAA TAAATATTCT CATTGTCAAT CAGAAAAAAA AAAAA          895

(2) INFORMATION FOR SEQ ID NO:26:

(i) SEQUENCE CHARACTERISTICS:
        (A) LENGTH: 936 base pairs
        (B) TYPE: nucleic acid
        (C) STRANDEDNESS: single
        (D) TOPOLOGY: linear (vii) IMMEDIATE SOURCE:
        (A) LIBRARY: SYNONOT01
        (B) CLONE: 3551457

(xi) SEQUENCE DESCRIPTION: SEQ ID NO:26:

CTCCTCAGAA GCCCCCAGAG CACAACTCCT TACCATGGAC TGGACCTGGA GGATCCTCTT      60

TTTGGTGGCA GCAGCCACAG GTGCCCACTC CCAGGTCCAG CTTGTGCAGT CTGGGGCTGA     120

GGTGAAGAAG CCTGGGGCCT CAGTGAAGGT TTCCTGCAAG ACTTCTGGAT ACATCATCAC     180

TAGTTATGCT ATGCATTGGG TGCGCCAGGC CCCCGGACAA AGGCTTGAGT GGATGGGATG     240

GATCAACGCT GGCAATGGTA ACACAAAATA TTCACAGAAC TTCCAGGGCA GAATCACCAT     300

TACCAGGGAC ACATCCGCGA GCACAGCCTA CATGGAGTTG AGCAGCCTGA GATCTGAAGA     360

CACGGCTGTG TATTACTGTG CGAGAGTCTG GGCTGGGGAA TTTACTAGCT TTGACTACTG     420

GGGCCAGGGA ACCCTGGTCA CCGTCTCCTC AGCATCCCCG ACCAGCCCCA AGGTCTTCCG     480

GCTGAGCCTC GAAAGAACCC CCAAGGATGG GAAACGTGGT CGTCGAATGC CTGGCCAAGG     540

GCTTCTTCCC CCAGGAGCCA CTCAGTGTGA CTTGGAGCGA AAAGGGNACA GGACCTTGAC     600

CGGCAAAAAA TTTTCCCGAC CTAGCCCAGG AATGCCTTCG GGGGGACCTG TAACACCCAG     660

GAACCAAGCA CGCTTGAACA CATGCGGGCC CAAAGAAAGT GGCCCCAGAA CGGGCGAAAT     720

TCCGTGGAAA ATTGGCCCAA CGTGAAGACC ACTTATGCAG CGGATTCCCC AAGCTCAAGG     780
```

```
GAGTGTATGC AATAGGTCAC ACTTGCCCAA GGTGTACGCA GCCAGTAATT ACAACATGTG      840

AGTATCACGC CGCCCGATGA TTAGGCGCCT AGTAACGGAG CACAGTATCA TTAGTGTGAG      900

CACATGGGCT ACACACGAGA TTAGGACGTG CGGTTG                                936
```

(2) INFORMATION FOR SEQ ID NO:27:

(i) SEQUENCE CHARACTERISTICS:
        (A) LENGTH: 147 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1122909

(xi) SEQUENCE DESCRIPTION: SEQ ID NO:27:

```
Met Ser Gln Thr Arg Asp Leu Gln Gly Gly Lys Ala Phe Gly Leu Leu
 1               5                  10                  15

Lys Ala Gln Gln Glu Glu Arg Leu Asp Glu Ile Asn Lys Gln Phe Leu
                20                  25                  30

Asp Asp Pro Lys Tyr Ser Ser Asp Glu Asp Leu Pro Ser Lys Leu Glu
            35                  40                  45

Gly Phe Lys Glu Lys Tyr Met Glu Phe Asp Leu Asn Gly Asn Gly Asp
    50                  55                  60

Ile Asp Ile Met Ser Leu Lys Arg Met Leu Glu Lys Leu Gly Val Pro
65                  70                  75                  80

Lys Thr His Leu Glu Leu Lys Lys Leu Ile Gly Glu Val Ser Ser Gly
                85                  90                  95

Ser Gly Glu Thr Phe Ser Tyr Pro Asp Phe Leu Arg Met Met Leu Gly
               100                 105                 110

Lys Arg Ser Ala Ile Leu Lys Met Ile Leu Met Tyr Glu Glu Lys Ala
           115                 120                 125

Arg Glu Lys Glu Lys Pro Thr Gly Pro Pro Ala Lys Lys Ala Ile Ser
       130                 135                 140

Glu Leu Pro
145
```

(2) INFORMATION FOR SEQ ID NO:28:

(i) SEQUENCE CHARACTERISTICS:
        (A) LENGTH: 346 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1550785

(xi) SEQUENCE DESCRIPTION: SEQ ID NO:28:

```
Met Gln Lys Gly Glu Thr Gly Lys Asn Leu Ser Ser Glu Asn Pro Lys
 1               5                  10                  15

Gln Met Gly Ala Pro Gly Phe Gln Gly Glu Gln Ala Met Trp Val Leu
                20                  25                  30

Pro Leu Tyr Ala Glu Gly Leu Asn Thr Ser Leu Ser Gln Arg Lys Ala
            35                  40                  45

Cys Val Ser Asp Ser Met Leu Pro His Leu Ile Leu Arg Leu Arg Gly
    50                  55                  60
```

-continued

```
Leu Gln Gly Pro Ala Asp Ala Pro Ala Glu Ala His Pro Ser Gly Gln
 65                  70                  75                  80

Asp Trp Asp Arg Gln Glu Cys His Trp Gln Gln His Pro Gly Ser Glu
                 85                  90                  95

Val Leu Pro Val Gln Ala Gly Gly Ala Cys His Gln Lys Leu His
            100                 105                 110

Phe Gly Gln Gln Asn Val Gly Arg Leu Ala Gly Gly Gly Gly His
            115                 120                 125

Pro Gly Tyr Leu Gln Leu Arg Asp Pro Ala Asp Arg Pro Trp Val Arg
            130                 135                 140

Gly Asp Ser Pro Leu Leu Cys Ala Val Gly Pro Trp Ala His Ala Leu
145                 150                 155                 160

Leu Leu Val Thr Gln Leu Gly Arg Phe Thr Met Gln Asp Ser Gln Ala
                165                 170                 175

Leu Ala Ala Val Lys Arg Leu Phe Gly Lys Gln Val Met Ala Arg Thr
                180                 185                 190

Val Val Val Phe Thr Arg Gln Glu Asp Leu Ala Gly Asp Ser Leu Gln
                195                 200                 205

Asp Tyr Val His Cys Thr Asp Asn Arg Ala Leu Arg Asp Leu Val Ala
        210                 215                 220

Glu Cys Gly Gly Arg Val Cys Ala Leu Asn Asn Arg Ala Thr Gly Ser
225                 230                 235                 240

Glu Arg Glu Ala Gln Ala Glu Gln Leu Leu Gly Met Val Ala Cys Leu
                245                 250                 255

Val Arg Glu His Gly Gly Ala His Tyr Ser Asn Glu Val Tyr Glu Leu
                260                 265                 270

Val Gln Asp Thr Arg Cys Ala Asp Pro Gln Asp Gln Val Ala Lys Val
            275                 280                 285

Ala Glu Ile Val Ala Glu Arg Met Gln Arg Arg Thr Arg Leu Leu Ala
            290                 295                 300

Gly Leu Trp Gly Trp Arg Lys Phe Tyr Trp Lys Gly Trp Arg Arg Gly
305                 310                 315                 320

Phe Ser Val Phe Leu Gly Val Ala Ile Leu Ile Tyr Leu Leu Phe Tyr
                325                 330                 335

Arg Lys Gly Phe Gly Asp Gln Asn Asn Arg
            340                 345
```